United States Patent
Dinville et al.

(10) Patent No.: US 9,937,050 B2
(45) Date of Patent: *Apr. 10, 2018

(54) VERTEBRAL IMPLANT, VERTEBRAL FASTENING DEVICE OF THE IMPLANT AND IMPLANT INSTRUMENTATION

(71) Applicant: LDR Medical, Rosières Près Troyes (FR)

(72) Inventors: Hervé Dinville, St Parres aux Tertres (FR); Samuel Lequette, Pessac (FR)

(73) Assignee: LDR Medical, Sainte-Savine (FR)

( * ) Notice: Subject to any disclaimer, the term of this patent is extended or adjusted under 35 U.S.C. 154(b) by 244 days.

This patent is subject to a terminal disclaimer.

(21) Appl. No.: 14/891,322

(22) PCT Filed: May 16, 2014

(86) PCT No.: PCT/EP2014/060135
§ 371 (c)(1),
(2) Date: Nov. 13, 2015

(87) PCT Pub. No.: WO2014/184367
PCT Pub. Date: Nov. 20, 2014

(65) Prior Publication Data
US 2016/0100953 A1    Apr. 14, 2016

(30) Foreign Application Priority Data
May 16, 2013    (FR) ...................................... 13 54421

(51) Int. Cl.
A61F 2/44    (2006.01)
A61F 2/46    (2006.01)
A61F 2/30    (2006.01)

(52) U.S. Cl.
CPC ................ *A61F 2/442* (2013.01); *A61F 2/44* (2013.01); *A61F 2/447* (2013.01); *A61F 2/4455* (2013.01);
(Continued)

(58) Field of Classification Search
CPC ............. A61F 2/44; A61F 2/442; A61F 2/443
See application file for complete search history.

(56) References Cited

U.S. PATENT DOCUMENTS 344,683 A    6/1886  Sherer
1,025,596 A  5/1912  Strawser
(Continued)

FOREIGN PATENT DOCUMENTS

FR    2916956    12/2008
FR    2954692    7/2011
(Continued)

OTHER PUBLICATIONS

Apparatus and Method for Fusing Opposing Spinal Vertebrae, Bramlet, Dale G. et al., U.S. Appl. No. 09/635,436, filed Aug. 11, 2000.
(Continued)

*Primary Examiner* — Christian Sevilla
(74) *Attorney, Agent, or Firm* — Lauff Law PLLC

(57) ABSTRACT

This disclosure provides vertebral implants, fastening devices for vertebral implants, and implant instrumentation, and various combinations thereof. In some embodiments, the implant comprises a peripheral wall extending according to a vertical axis between upper and lower surfaces of the implant, with each such surface configured to be placed in contact with a vertebral structure, respectively, at the top and the bottom of the vertebral segment replaced by the implant. Some embodiments comprise fastening means, deployment of which anchors the implant in the lower and upper
(Continued)

vertebral structures. Some fastening means may be deployed by sliding parallel to the vertical axis of the implant, and may comprise a plate with at least one part remaining in contact with the peripheral wall of the implant when deployed and a pointed end projecting from one of the upper and lower surfaces of the implant to enter a vertebral structures on completion of deployment.

19 Claims, 32 Drawing Sheets

(52) U.S. Cl.
CPC ..... *A61F 2/4611* (2013.01); *A61F 2002/3037* (2013.01); *A61F 2002/30176* (2013.01); *A61F 2002/30331* (2013.01); *A61F 2002/30372* (2013.01); *A61F 2002/30383* (2013.01); *A61F 2002/30448* (2013.01); *A61F 2002/30487* (2013.01); *A61F 2002/30497* (2013.01); *A61F 2002/30579* (2013.01); *A61F 2002/30599* (2013.01); *A61F 2002/30604* (2013.01); *A61F 2002/30777* (2013.01); *A61F 2002/30782* (2013.01); *A61F 2002/30784* (2013.01); *A61F 2002/30785* (2013.01); *A61F 2002/30841* (2013.01); *A61F 2002/448* (2013.01); *A61F 2002/4475* (2013.01); *A61F 2002/4622* (2013.01); *A61F 2220/0016* (2013.01); *A61F 2310/00011* (2013.01); *A61F 2310/00023* (2013.01)

(56) References Cited

U.S. PATENT DOCUMENTS

| | | |
|---|---|---|
| 1,121,484 A | 12/1914 | Crites |
| 3,875,595 A | 8/1975 | Froning |
| 3,948,262 A | 6/1976 | Zaffaroni |
| 4,135,506 A | 1/1979 | Ulrich |
| 4,349,921 A | 9/1982 | Kuntz |
| 4,507,115 A | 3/1985 | Kambara et al. |
| 4,790,303 A | 12/1988 | Steffee |
| 4,834,757 A | 5/1989 | Brantigan |
| 4,863,476 A | 9/1989 | Shepperd |
| 4,892,545 A | 1/1990 | Day et al. |
| 4,904,261 A | 2/1990 | Dove et al. |
| 5,108,442 A | 4/1992 | Smith |
| 5,192,327 A * | 3/1993 | Brantigan ............. A61F 2/44 606/247 |
| 5,326,205 A | 7/1994 | Anspach, Jr. et al. |
| 5,443,514 A | 8/1995 | Steffee |
| 5,501,695 A | 3/1996 | Anspach, Jr. et al. |
| 5,522,899 A | 6/1996 | Michelson |
| 5,571,109 A | 11/1996 | Bertagnoli |
| 5,609,635 A | 3/1997 | Michelson |
| 5,683,394 A | 4/1997 | Rinner |
| 5,658,335 A | 8/1997 | Allen |
| 5,776,199 A | 7/1998 | Michelson |
| 5,800,547 A | 9/1998 | Schafer et al. |
| 5,810,820 A | 9/1998 | Santori et al. |
| 5,849,004 A | 12/1998 | Bramlet |
| 5,888,228 A | 3/1999 | Knothe et al. |
| 5,976,139 A | 11/1999 | Bramlet |
| 6,066,175 A | 5/2000 | Henderson et al. |
| 6,099,531 A | 8/2000 | Bonutti |
| 6,102,950 A | 8/2000 | Vaccaro |
| 6,113,638 A | 9/2000 | Williams et al. |
| 6,143,032 A | 11/2000 | Schafer et al. |
| 6,174,311 B1 | 1/2001 | Branch et al. |
| 6,179,873 B1 | 1/2001 | Zientek |
| 6,183,474 B1 | 2/2001 | Bramlet et al. |
| 6,206,923 B1 | 3/2001 | Boyd et al. |
| 6,210,442 B1 | 3/2001 | Wing et al. |
| 6,231,610 B1 | 5/2001 | Geisler |
| 6,267,764 B1 | 7/2001 | Elberg |
| 6,258,089 B1 | 10/2001 | Campbell et al. |
| 6,302,914 B1 | 10/2001 | Michelson |
| 6,342,074 B1 | 1/2002 | Simpson |
| 6,371,987 B1 | 4/2002 | Weiland et al. |
| 6,383,186 B1 | 7/2002 | Michelson |
| 6,419,703 B1 | 7/2002 | Fallin et al. |
| 6,419,706 B1 | 7/2002 | Graf |
| 6,423,063 B1 | 7/2002 | Bonutti |
| 6,447,544 B1 | 9/2002 | Michelson |
| 6,447,546 B1 | 9/2002 | Bramlet et al. |
| 6,447,547 B1 | 9/2002 | Michelson |
| 6,471,724 B2 | 10/2002 | Zdeblick et al. |
| 6,478,823 B1 | 11/2002 | Michelson |
| 6,485,517 B1 | 11/2002 | Michelson |
| 6,500,205 B1 | 12/2002 | Michelson |
| 6,527,803 B1 | 4/2003 | Crozet et al. |
| 6,540,753 B2 | 4/2003 | Cohen |
| 6,558,423 B1 | 5/2003 | Michelson |
| 6,558,424 B2 | 5/2003 | Thalgott |
| 6,565,605 B2 | 5/2003 | Goble et al. |
| 6,607,530 B1 | 8/2003 | Carl et al. |
| 6,610,065 B1 | 8/2003 | Branch et al. |
| 6,620,163 B1 | 9/2003 | Michelson |
| 6,648,893 B2 | 11/2003 | Dudasik |
| 6,695,846 B2 | 2/2004 | Richelsoph et al. |
| 6,706,067 B2 | 3/2004 | Shimp et al. |
| 6,709,458 B2 | 3/2004 | Michelson |
| 6,712,818 B1 | 3/2004 | Michelson |
| 6,716,247 B2 | 4/2004 | Michelson |
| 6,723,128 B2 | 4/2004 | Uk |
| 6,733,535 B2 | 5/2004 | Michelson |
| 6,749,636 B2 | 6/2004 | Michelson |
| 6,767,367 B1 | 7/2004 | Michelson |
| 6,770,096 B2 | 8/2004 | Bolger et al. |
| 6,793,679 B2 | 9/2004 | Michelson |
| 6,805,714 B2 | 10/2004 | Sutcliffe |
| 6,808,537 B2 | 10/2004 | Michelson |
| 6,835,206 B2 | 12/2004 | Jackson |
| 6,849,093 B2 | 2/2005 | Michelson |
| 6,866,682 B1 * | 3/2005 | An ........................ A61F 2/44 623/17.11 |
| 6,890,355 B2 | 5/2005 | Michelson |
| 6,902,580 B2 | 6/2005 | Fallin et al. |
| 6,923,811 B1 | 8/2005 | Carl et al. |
| 6,923,830 B2 | 8/2005 | Michelson |
| 6,955,691 B2 | 10/2005 | Chae et al. |
| 6,962,606 B2 | 11/2005 | Michelson |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,994,727 B2 | 2/2006 | Khandkar et al. |
| 7,001,385 B2 | 2/2006 | Bonutti |
| 7,008,453 B1 | 3/2006 | Michelson |
| 7,033,394 B2 | 4/2006 | Michelson |
| 7,041,135 B2 | 5/2006 | Michelson |
| 7,041,136 B2 | 5/2006 | Goble et al. |
| 7,051,610 B2 | 5/2006 | Stoianovici et al. |
| 7,060,097 B2 | 6/2006 | Fraser et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,137,984 B2 | 11/2006 | Michelson |
| 7,153,325 B2 | 12/2006 | Kim et al. |
| 7,163,561 B2 | 1/2007 | Michelson |
| 7,192,447 B2 * | 3/2007 | Rhoda .................. A61F 2/44 623/17.11 |
| 7,303,583 B1 | 4/2007 | Schar et al. |
| 7,211,112 B2 | 5/2007 | Baynham et al. |

(56) References Cited

U.S. PATENT DOCUMENTS

| | | | |
|---|---|---|---|
| 7,217,291 | B2 | 5/2007 | Zucherman et al. |
| 7,217,293 | B2 | 5/2007 | Branch, Jr. |
| 7,223,289 | B2 | 5/2007 | Trieu et al. |
| 7,232,463 | B2 | 6/2007 | Falahee |
| 7,232,464 | B2 | 6/2007 | Mathieu et al. |
| 7,235,082 | B2 | 6/2007 | Bartish et al. |
| 7,238,205 | B2 | 7/2007 | Karahalios |
| 7,255,698 | B2 | 8/2007 | Michelson |
| 7,326,248 | B2 | 2/2008 | Michelson |
| 7,361,196 | B2 | 4/2008 | Fallin et al. |
| 7,410,501 | B2 | 8/2008 | Michelson |
| 7,431,735 | B2 | 10/2008 | Liu et al. |
| 7,435,262 | B2 | 10/2008 | Michelson |
| 7,442,209 | B2 | 10/2008 | Michelson |
| 7,445,635 | B2 | 11/2008 | Fallin et al. |
| 7,445,636 | B2 | 11/2008 | Michelson |
| 7,455,684 | B2 | 11/2008 | Gradel et al. |
| 7,455,692 | B2 | 11/2008 | Michelson |
| 7,465,317 | B2 | 12/2008 | Malberg et al. |
| 7,473,276 | B2 | 1/2009 | Aebi et al. |
| 7,503,933 | B2 | 3/2009 | Michelson |
| 7,540,882 | B2 | 6/2009 | Michelson |
| 7,544,208 | B1* | 6/2009 | Mueller ............ A61F 2/44 623/17.15 |
| 7,563,284 | B2 | 7/2009 | Coppes et al. |
| 7,563,286 | B2 | 7/2009 | Gerber et al. |
| 7,566,345 | B1 | 7/2009 | Fallin et al. |
| 7,588,590 | B2 | 9/2009 | Chervitz et al. |
| 7,591,851 | B2 | 9/2009 | Winslow et al. |
| 7,594,931 | B2 | 9/2009 | Louis et al. |
| 7,594,932 | B2 | 9/2009 | Aferzon et al. |
| 7,601,170 | B2 | 10/2009 | Winslow et al. |
| 7,604,654 | B2 | 10/2009 | Fallin et al. |
| 7,608,107 | B2 | 10/2009 | Michelson |
| 7,611,538 | B2 | 11/2009 | Belliard et al. |
| 7,618,453 | B2 | 11/2009 | Goble et al. |
| 7,618,455 | B2 | 11/2009 | Goble et al. |
| 7,618,456 | B2 | 11/2009 | Mathieu et al. |
| 7,621,955 | B2 | 11/2009 | Goble et al. |
| 7,621,958 | B2 | 11/2009 | Zdeblick et al. |
| 7,625,393 | B2 | 12/2009 | Fallin et al. |
| 7,637,951 | B2 | 12/2009 | Michelson |
| 7,637,953 | B2 | 12/2009 | Branch et al. |
| 7,637,954 | B2 | 12/2009 | Michelson |
| 7,641,690 | B2 | 1/2010 | Abdou |
| 7,655,027 | B2 | 2/2010 | Michelson |
| 7,658,766 | B2 | 2/2010 | Melkent et al. |
| 7,674,296 | B2* | 3/2010 | Rhoda ............ A61F 2/44 623/17.11 |
| 7,682,396 | B2 | 3/2010 | Beaurain et al. |
| 7,695,516 | B2 | 4/2010 | Zeegers |
| 7,695,517 | B2 | 4/2010 | Benzel et al. |
| 7,727,280 | B2 | 6/2010 | McLuen |
| 7,744,602 | B2 | 6/2010 | Teeny et al. |
| 7,749,252 | B2 | 7/2010 | Zucherman et al. |
| 7,749,274 | B2 | 7/2010 | Razian |
| 7,753,937 | B2 | 7/2010 | Chervitz et al. |
| 7,758,648 | B2* | 7/2010 | Castleman ............ A61F 2/4611 623/17.11 |
| 7,771,473 | B2 | 8/2010 | Thramann |
| 7,771,475 | B2 | 8/2010 | Michelson |
| 7,776,090 | B2 | 8/2010 | Winslow et al. |
| 7,780,670 | B2 | 8/2010 | Bonutti |
| 7,789,914 | B2 | 9/2010 | Michelson |
| 7,794,502 | B2 | 9/2010 | Michelson |
| 7,799,053 | B2 | 9/2010 | Haid, Jr. et al. |
| 7,799,057 | B2 | 9/2010 | Hudgins et al. |
| 7,799,081 | B2 | 9/2010 | McKinley |
| 7,811,326 | B2 | 10/2010 | Braddock, Jr. et al. |
| 7,819,903 | B2 | 10/2010 | Fraser et al. |
| 7,824,445 | B2 | 11/2010 | Biro et al. |
| 7,833,255 | B2 | 11/2010 | Chow et al. |
| 7,842,088 | B2 | 11/2010 | Rashbaum et al. |
| 7,846,188 | B2 | 12/2010 | Moskowitz et al. |
| 7,846,207 | B2 | 12/2010 | Lechmann et al. |
| 7,850,731 | B2 | 12/2010 | Brittan et al. |
| 7,850,732 | B2 | 12/2010 | Heinz |
| 7,850,733 | B2 | 12/2010 | Baynham et al. |
| 7,862,616 | B2 | 1/2011 | Lechmann et al. |
| 7,871,441 | B2 | 1/2011 | Eckman |
| 7,875,076 | B2 | 1/2011 | Mathieu et al. |
| 7,887,591 | B2 | 2/2011 | Aebi et al. |
| 7,892,261 | B2 | 2/2011 | Bonutti |
| 7,892,286 | B2 | 2/2011 | Michelson |
| 7,909,871 | B2 | 3/2011 | Abdou |
| 7,914,560 | B2 | 3/2011 | Hoy et al. |
| 7,922,729 | B2 | 4/2011 | Michelson |
| 7,931,674 | B2 | 4/2011 | Zucherman et al. |
| 7,931,840 | B2 | 4/2011 | Michelson |
| 7,935,149 | B2 | 5/2011 | Michelson |
| 7,951,198 | B2 | 5/2011 | Sucec et al. |
| 7,955,390 | B2 | 6/2011 | Fallin et al. |
| 7,972,337 | B2 | 7/2011 | Boyajian et al. |
| 7,972,363 | B2 | 7/2011 | Moskowitz et al. |
| 7,972,365 | B2 | 7/2011 | Michelson |
| 7,976,566 | B2 | 7/2011 | Michelson |
| 7,985,255 | B2 | 7/2011 | Bray et al. |
| 7,985,258 | B2 | 7/2011 | Zdeblick et al. |
| 7,993,373 | B2 | 8/2011 | Hoy et al. |
| 7,998,177 | B2 | 8/2011 | Hoy et al. |
| 7,998,178 | B2 | 8/2011 | Hoy et al. |
| 7,998,211 | B2 | 8/2011 | Baccelli et al. |
| 8,007,534 | B2 | 8/2011 | Michelson |
| 8,021,401 | B2 | 9/2011 | Carl et al. |
| 8,021,430 | B2 | 9/2011 | Michelson |
| 8,043,334 | B2 | 10/2011 | Fisher et al. |
| 8,062,336 | B2 | 11/2011 | Triplett et al. |
| 8,062,375 | B2 | 11/2011 | Glerum et al. |
| 8,066,741 | B2 | 11/2011 | Fallin et al. |
| 8,066,749 | B2 | 11/2011 | Winslow et al. |
| 8,070,816 | B2 | 12/2011 | Taylor |
| 8,070,819 | B2 | 12/2011 | Aferzon et al. |
| 8,075,593 | B2 | 12/2011 | Hess |
| 8,075,618 | B2 | 12/2011 | Trieu et al. |
| 8,075,621 | B2 | 12/2011 | Michelson |
| 8,080,062 | B2 | 12/2011 | Armstrong et al. |
| 8,097,034 | B2 | 1/2012 | Michelson |
| 8,114,082 | B2 | 2/2012 | Boyajian et al. |
| 8,118,873 | B2 | 2/2012 | Humphreys et al. |
| 8,137,405 | B2 | 3/2012 | Kostuik et al. |
| 8,147,556 | B2 | 4/2012 | Louis et al. |
| 8,257,443 | B2 | 4/2012 | Kamran et al. |
| 8,167,946 | B2 | 5/2012 | Michelson |
| 8,167,949 | B2 | 5/2012 | Tyber et al. |
| 8,167,950 | B2 | 5/2012 | Aferzon et al. |
| 8,182,539 | B2 | 5/2012 | Tyber et al. |
| 8,187,329 | B2 | 5/2012 | Theofilos |
| 8,187,332 | B2 | 5/2012 | McLuen |
| 8,303,663 | B2 | 6/2012 | Jimenez et al. |
| 8,216,312 | B2 | 7/2012 | Gray |
| 8,241,363 | B2* | 8/2012 | Sommerich ............ A61F 2/4611 606/57 |
| 8,267,999 | B2 | 9/2012 | Beaurain et al. |
| 8,313,528 | B1 | 11/2012 | Wensel |
| 8,323,345 | B2 | 12/2012 | Sledge |
| 8,343,197 | B2 | 1/2013 | Gonzalez-Hernandez |
| 8,343,219 | B2 | 1/2013 | Allain et al. |
| 8,349,015 | B2 | 1/2013 | Bae et al. |
| 8,545,563 | B2 | 1/2013 | Brun et al. |
| 8,460,388 | B2 | 6/2013 | Irwan et al. |
| 8,535,352 | B2 | 9/2013 | Altarac et al. |
| 8,617,245 | B2 | 12/2013 | Brett |
| 8,696,681 | B2 | 4/2014 | Harris et al. |
| 8,979,932 | B2 | 3/2015 | Rashbaum et al. |
| 9,039,774 | B2 | 5/2015 | Chataigner et al. |
| 9,044,337 | B2 | 6/2015 | Dinville et al. |
| 9,078,765 | B2 | 7/2015 | Louis et al. |
| 2002/0016592 | A1 | 2/2002 | Branch et al. |
| 2002/0026243 | A1 | 2/2002 | Lin |
| 2002/0040243 | A1 | 4/2002 | Attali et al. |
| 2002/0059938 | A1 | 5/2002 | Fogarty et al. |
| 2002/0070565 | A1 | 6/2002 | Szapucki et al. |
| 2002/0099443 | A1* | 7/2002 | Messerli ............ A61F 2/30744 623/17.11 |

(56) References Cited

U.S. PATENT DOCUMENTS

| | | |
|---|---|---|
| 2002/0161444 A1 | 10/2002 | Choi |
| 2002/0165613 A1 | 11/2002 | Lin et al. |
| 2002/0193880 A1 | 12/2002 | Fraser |
| 2003/0032957 A1* | 2/2003 | McKinley .......... A61B 17/7032 606/266 |
| 2003/0069640 A1 | 4/2003 | Ferreira et al. |
| 2003/0074075 A1 | 4/2003 | Thomas, Jr. et al. |
| 2003/0135279 A1 | 7/2003 | Michelson |
| 2003/0149484 A1 | 7/2003 | Michelson |
| 2003/0181913 A1* | 9/2003 | Lieberman ......... A61B 17/1604 606/325 |
| 2003/0187436 A1 | 10/2003 | Bolger et al. |
| 2003/0191531 A1* | 10/2003 | Berry .................. A61F 2/44 623/17.11 |
| 2003/0195514 A1 | 10/2003 | Trieu et al. |
| 2004/0010312 A1 | 1/2004 | Enayati |
| 2004/0030387 A1 | 2/2004 | Landry et al. |
| 2004/0073307 A1 | 4/2004 | Keller |
| 2004/0073313 A1 | 4/2004 | Link et al. |
| 2004/0117022 A1 | 6/2004 | Marnay et al. |
| 2004/0122518 A1* | 6/2004 | Rhoda .................. A61F 2/44 623/17.11 |
| 2004/0186569 A1* | 9/2004 | Berry .................. A61F 2/44 623/17.11 |
| 2004/0199254 A1 | 10/2004 | Louis et al. |
| 2004/0210219 A1 | 10/2004 | Bray |
| 2004/0210227 A1 | 10/2004 | Trail et al. |
| 2004/0210313 A1 | 10/2004 | Michelson |
| 2004/0243238 A1 | 12/2004 | Arnin et al. |
| 2004/0243240 A1 | 12/2004 | Beaurain et al. |
| 2004/0254643 A1 | 12/2004 | Jackson |
| 2005/0015149 A1 | 1/2005 | Michelson |
| 2005/0027359 A1 | 2/2005 | Mashburn |
| 2005/0038512 A1 | 2/2005 | Michelson |
| 2005/0027362 A1 | 3/2005 | Williams et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0085917 A1 | 4/2005 | Marnay et al. |
| 2005/0096745 A1 | 5/2005 | Andre et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0159814 A1* | 7/2005 | Karahalios ............. A61F 2/44 623/17.11 |
| 2005/0177236 A1 | 8/2005 | Mathieu et al. |
| 2005/0209697 A1* | 9/2005 | Paponneau ............. A61F 2/44 623/17.15 |
| 2005/0216081 A1* | 9/2005 | Taylor ................. A61F 2/44 623/17.11 |
| 2005/0283236 A1 | 12/2005 | Razian |
| 2005/0288788 A1 | 12/2005 | Dougherty-Shah |
| 2006/0058878 A1 | 3/2006 | Michelson |
| 2006/0069437 A1 | 3/2006 | Weber |
| 2006/0085071 A1 | 4/2006 | Lechmann et al. |
| 2006/0085076 A1 | 4/2006 | Krishna et al. |
| 2006/0089717 A1 | 4/2006 | Krishna et al. |
| 2006/0095136 A1 | 5/2006 | McLuen |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0142863 A1 | 6/2006 | Fraser et al. |
| 2006/0155377 A1 | 7/2006 | Beaurain et al. |
| 2006/0276899 A1 | 7/2006 | Zipnick et al. |
| 2006/0206208 A1 | 9/2006 | Michelson |
| 2006/0235426 A1 | 10/2006 | Lim et al. |
| 2006/0241621 A1 | 10/2006 | Moskowitz et al. |
| 2006/0241761 A1 | 10/2006 | Gately |
| 2006/0241764 A1 | 10/2006 | Michelson |
| 2006/0253201 A1 | 11/2006 | McLuen |
| 2007/0016297 A1 | 1/2007 | Johnson |
| 2007/0049943 A1 | 1/2007 | Moskowitz et al. |
| 2007/0032871 A1 | 2/2007 | Michelson |
| 2007/0073404 A1 | 3/2007 | Rashbaum et al. |
| 2007/0093850 A1 | 4/2007 | Harris et al. |
| 2007/0142843 A1 | 6/2007 | Dye |
| 2007/0208345 A1 | 6/2007 | Marnay et al. |
| 2007/0162128 A1 | 7/2007 | DeRidder et al. |
| 2007/0179623 A1 | 8/2007 | Trieu et al. |
| 2007/0106388 A1 | 10/2007 | Michelson |
| 2007/0233253 A1 | 10/2007 | Bray et al. |
| 2007/0250167 A1 | 10/2007 | Bray et al. |
| 2007/0260249 A1 | 11/2007 | Boyajian et al. |
| 2007/0270954 A1 | 11/2007 | Wu |
| 2007/0270960 A1 | 11/2007 | Bonin et al. |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0027547 A1 | 1/2008 | Yu et al. |
| 2008/0027550 A1 | 1/2008 | Link et al. |
| 2008/0033562 A1 | 2/2008 | Krishna et al. |
| 2008/0132949 A1 | 5/2008 | Aferzon et al. |
| 2008/0033432 A1 | 7/2008 | McGraw et al. |
| 2008/0177306 A1 | 7/2008 | Lamborne et al. |
| 2008/0195211 A1 | 8/2008 | Lin et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281424 A1* | 11/2008 | Parry .................... A61F 2/4455 623/17.16 |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0054988 A1 | 2/2009 | Hess |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0138086 A1 | 5/2009 | Dewey |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216331 A1 | 8/2009 | Grotz et al. |
| 2009/0222092 A1 | 9/2009 | Davis et al. |
| 2009/0222100 A1 | 9/2009 | Cipoletti et al. |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0016903 A1 | 1/2010 | Matityahu et al. |
| 2010/0016974 A1 | 1/2010 | Janowski et al. |
| 2010/0049259 A1 | 2/2010 | Lambrecht et al. |
| 2010/0050276 A1 | 2/2010 | DePaepe |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |

(56) References Cited

U.S. PATENT DOCUMENTS

| | | | |
|---|---|---|---|
| 2010/0179656 A1* | 7/2010 | Theofilos | A61F 2/44 623/17.11 |
| 2010/0185289 A1 | 7/2010 | Kirwan et al. | |
| 2010/0204796 A1 | 8/2010 | Bae et al. | |
| 2010/0211108 A1 | 8/2010 | Lemole, Jr. | |
| 2010/0211176 A1 | 8/2010 | Greenhalgh | |
| 2010/0217393 A1 | 8/2010 | Theofilos | |
| 2010/0234958 A1 | 9/2010 | Linares | |
| 2010/0249935 A1 | 9/2010 | Slivka et al. | |
| 2010/0249937 A1 | 9/2010 | Blain et al. | |
| 2010/0280618 A1 | 11/2010 | Jodaitis et al. | |
| 2010/0286777 A1 | 11/2010 | Errico et al. | |
| 2010/0286787 A1 | 11/2010 | Villiers et al. | |
| 2010/0298941 A1 | 11/2010 | Hes et al. | |
| 2010/0305700 A1 | 12/2010 | Ben-Arye et al. | |
| 2010/0305704 A1 | 12/2010 | Messerli et al. | |
| 2010/0312344 A1 | 12/2010 | Reiley | |
| 2010/0312345 A1 | 12/2010 | Duffield et al. | |
| 2010/0312346 A1 | 12/2010 | Kueenzi et al. | |
| 2011/0004310 A1 | 1/2011 | Michelson | |
| 2011/0009966 A1 | 1/2011 | Michelson | |
| 2011/0015745 A1 | 1/2011 | Bucci | |
| 2011/0035007 A1 | 2/2011 | Patel et al. | |
| 2011/0040382 A1 | 2/2011 | Muhanna | |
| 2011/0054616 A1 | 3/2011 | Kamran et al. | |
| 2011/0077738 A1 | 3/2011 | Ciupik et al. | |
| 2011/0077739 A1 | 3/2011 | Rashbaum et al. | |
| 2011/0082553 A1 | 4/2011 | Abdou | |
| 2011/0087327 A1 | 4/2011 | Lechmann et al. | |
| 2011/0093077 A1 | 4/2011 | Aebi et al. | |
| 2011/0098747 A1* | 4/2011 | Donner | A61B 17/70 606/264 |
| 2011/0118843 A1 | 5/2011 | Mathieu et al. | |
| 2011/0125267 A1 | 5/2011 | Michelson | |
| 2011/0137420 A1 | 6/2011 | Michelson | |
| 2011/0144703 A1 | 6/2011 | Krause et al. | |
| 2011/0160860 A1 | 6/2011 | Johnston et al. | |
| 2011/0166655 A1 | 7/2011 | Michelson | |
| 2011/0166656 A1 | 7/2011 | Thalgott et al. | |
| 2011/0166657 A1 | 7/2011 | Thalgott et al. | |
| 2011/0166658 A1 | 7/2011 | Garber et al. | |
| 2011/0172774 A1 | 7/2011 | Varela | |
| 2011/0178599 A1 | 7/2011 | Brett | |
| 2011/0196492 A1 | 8/2011 | Lambrecht et al. | |
| 2011/0196493 A1 | 8/2011 | Pimenta | |
| 2011/0196494 A1 | 8/2011 | Yedlicka et al. | |
| 2011/0202136 A1 | 8/2011 | Brittan et al. | |
| 2011/0208311 A1 | 8/2011 | Janowski | |
| 2011/0208313 A1 | 8/2011 | Michelson | |
| 2011/0230969 A1 | 9/2011 | Biedermann et al. | |
| 2011/0230971 A1 | 9/2011 | Donner et al. | |
| 2011/0264227 A1 | 10/2011 | Boyajian et al. | |
| 2011/0112587 A1 | 12/2011 | Patel et al. | |
| 2011/0295371 A1 | 12/2011 | Moskowitz et al. | |
| 2011/0301713 A1 | 12/2011 | Theofilos | |
| 2011/0301714 A1 | 12/2011 | Theofilos | |
| 2011/0313528 A1 | 12/2011 | Laubert et al. | |
| 2012/0022654 A1 | 1/2012 | Farris et al. | |
| 2012/0078371 A1 | 3/2012 | Gamache et al. | |
| 2012/0191196 A1 | 7/2012 | Louis et al. | |
| 2012/0197403 A1* | 8/2012 | Merves | A61F 2/44 623/17.16 |
| 2012/0197404 A1* | 8/2012 | Brun | A61F 2/447 623/17.16 |
| 2012/0265259 A1* | 10/2012 | LaPosta | A61B 17/8894 606/86 A |
| 2013/0123926 A1 | 5/2013 | Bae et al. | |
| 2013/0150968 A1 | 6/2013 | Dinville et al. | |
| 2013/0166029 A1 | 6/2013 | Dinville et al. | |
| 2013/0226300 A1* | 8/2013 | Chataigner | A61F 2/442 623/17.16 |
| 2013/0245767 A1* | 9/2013 | Lee | A61F 2/447 623/17.16 |
| 2015/0051702 A1 | 2/2015 | Chataigner et al. | |
| 2015/0127107 A1 | 5/2015 | Kim et al. | |
| 2015/0209089 A1 | 7/2015 | Chataigner et al. | |
| 2016/0058564 A1 | 3/2016 | Zappacosta et al. | |
| 2016/0058565 A1 | 3/2016 | Zappacosta et al. | |
| 2016/0100953 A1* | 4/2016 | Dinville | A61F 2/44 623/17.16 |
| 2017/0252182 A1* | 9/2017 | Acosta | A61F 2/4455 |
| 2017/0311997 A1* | 11/2017 | Lequette | A61B 17/72 |

FOREIGN PATENT DOCUMENTS

| | | |
|---|---|---|
| FR | 3005569 | 11/2014 |
| FR | 3020756 | 11/2015 |
| WO | WO0049977 | 8/2000 |
| WO | WO2006026425 | 3/2006 |
| WO | WO2008150724 | 12/2008 |
| WO | WO2013062716 | 5/2013 |

OTHER PUBLICATIONS

Intervertebral nucleus prosthesis and surgical procedure for implanting the same, Gau, Michel, U.S. Appl. No. 10/060,862, filed Jan. 30, 2002.

Intersomatic cage with unified grafts, Huppert, Jean, U.S. Appl. No. 10/276,712, filed Mar. 26, 2003.

Spinal Osteosynthesis Device and Preparation Method, Beaurain, Jacques et al., U.S. Appl. No. 10/473,999, filed Apr. 12, 2004.

Intervertebral Disc Prosthesis and Fitting Tools, Beaurain, Jacques et al., U.S. Appl. No. 10/476,565, filed Jun. 8, 2004.

Vertebral Cage Device With Modular Fixation, Louis, Christian et al., U.S. Appl. No. 10/483,563, filed May 21, 2004.

Progressive approach osteosynthesis device and preassembly method, Delecrin, Joel et al., U.S. Appl. No. 10/492,753, filed Aug. 9, 2004.

Plate for osteosynthesis device and method of preassembling such device, Delecrin, Joel et al., U.S. Appl. No. 10/492,827, filed Jul. 15, 2004.

Osseous anchoring device for a prosthesis, Huppert, Jean et al., U.S. Appl. No. 10/494,418, filed Jul. 22, 2004.

Implant for Osseous Anchoring with Polyaxial Head, Beaurain, Jacques et al., U.S. Appl. No. 10/498,234, filed Dec. 7, 2004.

Intervertebral Disc Prosthesis, Beaurain, Jacques et al., U.S. Appl. No. 10/533,846, filed Nov. 11, 2005.

Osseous anchoring implant with a polyaxial head and method for installing the implant, Renaud, Christian et al., U.S. Appl. No. 10/570,080, filed Jun. 9, 2006.

Device and method for sectioning a vertebral lamina, Mangione, Paolo, U.S. Appl. No. 10/575,065, filed May 30, 2006.

Intervertebral Disc Prosthesis, Hovorka, Istvan et al., U.S. Appl. No. 11/051,710, filed Feb. 4, 2005.

Intervertebral Disc Prosthesis, Zeegers, M. Willem, U.S. Appl. No. 11/098,266, filed Apr. 4, 2005.

Intervertebral Disc Prosthesis, Zeegers, Willem, U.S. Appl. No. 11/109,276, filed Apr. 18, 2005.

Instrumentation and Methods for Inserting an Intervertebral Disc Prosthesis, Dinville, Herve, U.S. Appl. No. 11/180,868, filed Jul. 13, 2005.

Intervertebral Disc Prosthesis, Rashbaum, Ralph et al., U.S. Appl. No. 11/341,007, filed Jan. 27, 2006.

Intervertebral Disc Prosthesis and Instrumentation for Insertion of the Prosthesis Between the Vertebrae, Rashbaum, Ralph et al., U.S. Appl. No. 11/362,253, filed Feb. 24, 2006.

Transforaminal intersomatic cage for an intervertebral fusion graft and an instrument for implanting the cage, Davis, Reginald James et al., U.S. Appl. No. 11/378,165, filed Mar. 17, 2006.

Intervertebral nucleus prosthesis and surgical procedure for implanting the same, Gau, Michel, U.S. Appl. No. 11/390,711, filed Mar. 27, 2006.

Intervertebral disc prosthesis insertion assemblies, Jodaitis, Alexandre et al., U.S. Appl. No. 11/676,237, filed Feb. 16, 2007.

Intersomatic cage with unified grafts, Huppert, Jean, U.S. Appl. No. 11/767,386, filed Jun. 22, 2007.

(56) References Cited

OTHER PUBLICATIONS

Nucleus Prostheses, Vila, Thierry et al., U.S. Appl. No. 11/874,144, filed Oct. 17, 2007.
Vertebral Support Device, Cho, Paul et al., U.S. Appl. No. 11/958,285, filed Dec. 17, 2007.
Intervertebral disc prosthesis, surgical methods, and fitting tools, Beaurain, Jacques et al., U.S. Appl. No. 12/025,677, filed Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Interveterbral disc prosthesis insertion assemblies, Jodaitis, Alexandre et al., U.S. Appl. No. 12/527,373, filed Mar. 19, 2010.
Intervertebral implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Herve et al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant, Intervertebral Implant and Implantation Instruments, Dinville, Hervé et al., U.S. Appl. No. 13/520,041, filed Nov. 26, 2012.
Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, Willem, U.S. Appl. No. 13/603,043, filed Sep. 4, 2012.
Intervertebral Disc Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforaminal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Intervertebral Disc Prosthesis Insertion Assemblies, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Instrument for Implanting an Interspinous Implant, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prosthesis, Vila, Thierry et al., U.S. Appl. No. 14/159,161, filed Jan. 20, 2014.
Interveterbral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.
Interspinous Implant and Instrument for Implanting an Interspinous Implant, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disc Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Cage Having Spike, Kim, Seo-Kon et al., U.S. Appl. No. 14/460,536, filed Aug. 15, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
Plate for osteosynthesis device and preassembly method, Delecrin, Joel et al., U.S. Appl. No. 14/584,674, filed Dec. 29, 2014.
Intervertebral Implant Having Extendable Bone Fixation Members, Brett, Darrell C., U.S. Appl. No. 14/594,770, filed Jan. 12, 2015.
Vertebral implant, device for vertebral attachment of the implant and instrumentation for implantation thereof, Ameil, Marc et al., U.S. Appl. No. 14/638,746, filed Mar. 4, 2015.
Intervertebral Disc Prosthesis, Zeegers, Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, Willem, U.S. Appl. No. 14/726,557, filed May 31, 2015.
Anchoring Device and System for an Intervertebral Implant, Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.

(56) References Cited

OTHER PUBLICATIONS

Instruments and Methods for Removing Fixation Devices from Intervertebral Implants, Dinville, Herve et al., U.S. Appl. No. 14/931,007, filed Nov. 3, 2015.

Instrumentation and Methods for Inserting an Intervertebral Disc Prosthesis, Dinville, Herve, U.S. Appl. No. 15/012,815, filed Feb. 1, 2016.

Intervertebral Disc Prosthesis, Beaurain, Jacques et al., U.S. Appl. No. 15/049,934, filed Feb. 22, 2016.

Intervertebral Disc Prosthesis and Instrumentation for Insertion of the Prosthesis Between the Vertebrae, Steib, Jean-Paul, U.S. Appl. No. 15/049,995, filed Feb. 22, 2016.

Anchoring device for a spinal implant, spinal implant and implantation instrumentation, Chataigner, Hervé et al., U.S. Appl. No. 15/115,659, filed Jul. 29, 2016.

Interspinous Implant and Implantation Instrument, Dinville, Herve et al., U.S. Appl. No. 15/145,413, filed May 3, 2016.

Implant for Osseous Anchoring with Polyaxial Head, Beaurain, Jacques et al., U.S. Appl. No. 15/145,431, filed May 3, 2016.

Intervertebral disc prosthesis, surgical methods, and fitting tools, Beaurain, Jacques et al., U.S. Appl. No. 15/150,316, filed May 9, 2016.

Interspinous Implant and Instrument for Implanting an Interspinous Implant, Dinville, Herve et al., U.S. Appl. No. 15/225,612, filed Aug. 1, 2016.

Intervertebral Disc Prosthesis, Zeegers, M. Willem, U.S. Appl. No. 15/269,923, filed Sep. 19, 2016.

Intervertebral Implant Having Extendable Bone Fixation Members, Brett, Darrell C., U.S. Appl. No. 15/289,861, filed Oct. 10, 2016.

Vertebral implant, device for vertebral attachment of the implant and instrumentation for implantation thereof, Ameil, Marc et al., U.S. Appl. No. 15/309,197, filed Nov. 6, 2016.

Intervertebral Disc Prosthesis Insertion Assemblies, Jodaitis, Alexandre et al., U.S. Appl. No. 15/340,565, filed Nov. 1, 2016.

Nucleus Prosthesis, Vila, Thierry et al., U.S. Appl. No. 15/391,305, filed Dec. 27, 2016.

Plate for osteosynthesis device and preassembly method, Delecrin, Joel et al., U.S. Appl. No. 15/414,523, filed Jan. 24, 2017.

Implant for Osseous Anchoring with Polyaxial Head, Beaurain, Jacques et al., U.S. Appl. No. 15/426,938, filed Feb. 7, 2017.

Intervertebral Disc Prosthesis, Zeegers, Willem, U.S. Appl. No. 15/432,795, filed Feb. 14, 2017.

System of spinal arthodesis implants, Mercier, Alexis et al., U.S. Appl. No. 15/442,591, filed Feb. 24, 2017.

Intervertebral Disc Prosthesis, Rashbaum, Ralph et al., U.S. Appl. No. 15/464,639, filed Mar. 21, 2017.

Transforaminal intersomatic cage for an intervertebral fusion graft and an instrument for implanting the cage, Davis, Reginald James et al., U.S. Appl. No. 15/465,143, filed Mar. 21, 2017.

Bone Implants, Lavigne, Christophe et al., U.S. Appl. No. 15/501,166, filed Feb. 1, 2017.

Bone anchoring system, associated implant and instrumentation, Lequette, Samuel et al., U.S. Appl. No. 15/582,568, filed Apr. 28, 2017.

Vertebral System, Implant and Inserts for Vertebral System, Joly, Florian et al., U.S. Appl. No. 15/586,003, filed May 3, 2017.

Vertebral Cage Device With Modular Fixation, Louis, Christian et al., U.S. Appl. No. 15/597,130, filed May 16, 2017.

Intervertebral Disc Prosthesis, Hovorka, Istvan et al., U.S. Appl. No. 15/603,429, filed May 23, 2017.

Transforaminal intersomatic cage for an intervertebral fusion graft and an instrument for implanting the cage, Davis, Reginald James et al., U.S. Appl. No. 15/659,602, filed Jul. 25, 2017.

Vertebral Support Device, Cho, Paul et al., U.S. Appl. No. 15/677,310, filed Aug. 15, 2017.

Intervertebral Implant Having Extendable Bone Fixation Members, Brett, Darrell C., U.S. Appl. No. 15/682,549, filed Aug. 22, 2017.

Anchoring Device and System for an Intervertebral Implant, Intervertebral Implant and Implantation Instrument, Dinville, Hervé et al., U.S. Appl. No. 15/708,860, filed Sep. 19, 2017.

Spinal Osteosynthesis Device and Preparation Method, Beaurain, Jacques et al., U.S. Appl. No. 15/708,907, filed Sep. 19, 2017.

Cage Having Spike, Kim, Seo-Kon et al., U.S. Appl. No. 15/723,174, filed Oct. 3, 2017.

Intervertebral disc prosthesis, surgical methods, and fitting tools, Beaurain, Jacques et al., U.S. Appl. No. 15/784,559, filed Oct. 16, 2017.

Intersomatic cage, intervertebral prosthesis, anchoring device and implantation instruments, Allain, Jerome et al., U.S. Appl. No. 15/792,123, filed Oct. 24, 2017.

Expansible Intervertebral Implant, Bernard, Pierre et al., U.S. Appl. No. 15/796,732, filed Oct. 27, 2017.

Expansible Intersomatic Cage, Bernard, Pierre et al., U.S. Appl. No. 15/796,733, filed Oct. 27, 2017.

Expansible Intersomatic Cage, Bernard, Pierre et al., U.S. Appl. No. 15/796,735, filed Oct. 27, 2017.

Intervertebral Fusion Cage with Retractable-Extrudable Pins, Brett, Darrell C., U.S. Appl. No. 61/243,297, filed Sep. 17, 2009.

Intervertebral Fusion Cage with Retractable-Extrudable Pins, Brett, Darrell C., U.S. Appl. No. 61/260,364, filed Nov. 11, 2009.

China State Intellectual Property Office; Search Report for Pub'n No. CN105208975, Application No. CN201480028167; dated May 16, 2016; China State Intellectual Property Office; Beijing, China; all pages.

China State Intellectual Property Office; Office Action for Pub'n No. CN105208975, Application No. CN201480028167; dated May 26, 2016; China State Intellectual Property Office; Beijing, China; all pages.

National Institute of Industrial Property (France); Search Report in Fench Pub. No. FR3005569, App. No. FR1354421; dated Feb. 12, 2014; National Institute of Industrial Property (France); France; all pages.

World Intellectual Property Organization; International Search Report and Written Opinion of the International Searching Authority for International App. No. WO2014184367, PCT Pub'n No. PCT/EP2014/060135; dated Aug. 26, 2014; WIPO; Geneva, Switzerland; all pages.

World Intellectual Property Organization; Response to Written Opinion of ISA for International App. No. WO2014184367, PCT Pub'n No. PCT/EP2014/060135; dated Jun. 27, 2016; WIPO; Geneva, Switzerland; all pages.

World Intellectual Property Organization; International Preliminary Report on Patentability for International App. No. WO2014184367, PCT Pub'n No. PCT/EP2014/060135; dated Sep. 18, 2015; WIPO; Geneva, Switzerland; all pages.

U.S. Patent & Trademark Office; Office Action in U.S. Appl. No. 14/246,442; dated Nov. 1, 2016; USPTO; Alexandria, Virgina; All Pages.

LDR Medical, by its attorneys; Reply to Office Action in U.S. Appl. No. 14/246,442; dated Feb. 1, 2017; USPTO; Alexandria, Virgina; All Pages.

U.S. Patent & Trademark Office; Office Action in U.S. Appl. No. 14/246,442; dated Mar. 6, 2017; USPTO; Alexandria, Virgina; All Pages.

LDR Medical, by its attorneys; Reply to Office Action in U.S. Appl. No. 14/246,442; dated Jun. 6, 2017; USPTO; Alexandria, Virgina; All Pages.

U.S. Patent & Trademark Office; Office Action in U.S. Appl. No. 14/246,442; dated Aug. 15, 2017; USPTO; Alexandria, Virgina; All Pages.

LDR Medical, by its attorneys; Reply to Office Action in U.S. Appl. No. 14/246,442; dated Nov. 15, 2017; USPTO; Alexandria, Virginia; All Pages.

World Intellectual Property Organization; International Search Report and Written Opinion of the International Searching Authority for International App. No. WO2015169878, PCT Pub'n No. PCT/EP2015/060001; dated Oct. 2, 2016; WIPO; Geneva, Switzerland; all pages.

World Intellectual Property Organization; International Preliminary Report on Patentability for International App. No. WO2015169878, PCT Pub'n No. PCT/EP2015/060001; dated Nov. 8, 2016; WIPO; Geneva, Switzerland; all pages.

(56) References Cited

OTHER PUBLICATIONS

National Institute of Industrial Property (France); Search Report in Fench Pub. No. FR3020756, App. No. FR1454102; dated Jan. 29, 2015; National Institute of Industrial Property (France); France; all pages.
U.S. Patent & Trademark Office; Office Action in U.S. Appl. No. 14/638,746; dated Jun. 13, 2017; USPTO; Alexandria, Virgina; All Pages.
LDR Medical, by its attorneys; Reply to Office Action in U.S. Appl. No. 14/638,746; dated Sep. 13, 2017; USPTO; Alexandria, Virgina; All Pages.
U.S. Patent & Trademark Office; Office Action in U.S. Appl. No. 14/638,746; dated Oct. 12, 2017; USPTO; Alexandria, Virgina; All Pages.

\* cited by examiner

Figure 17A
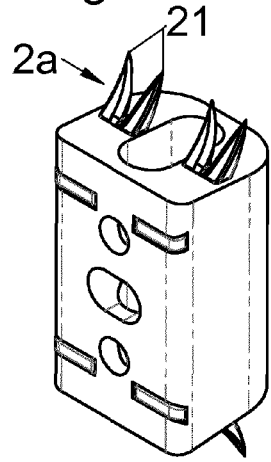
Figure 17B
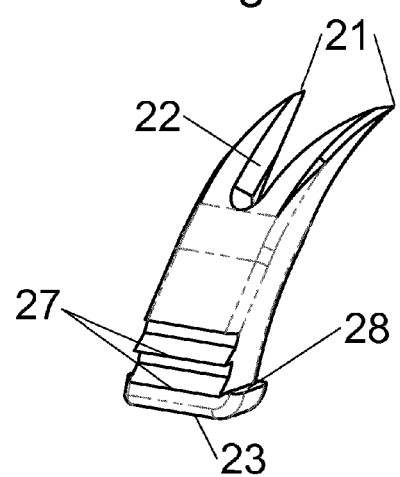
Figure 17C   Figure 17D   Figure 17E
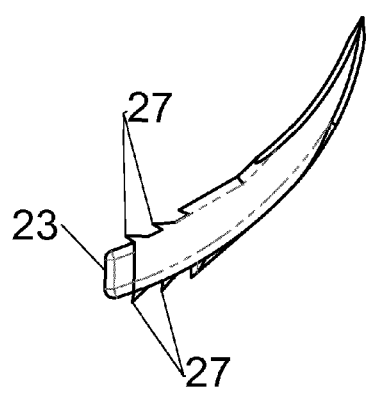 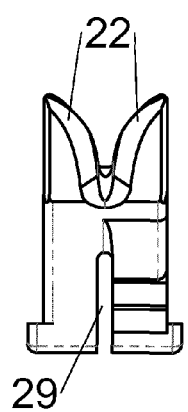 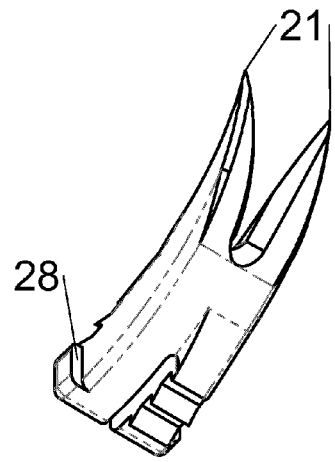

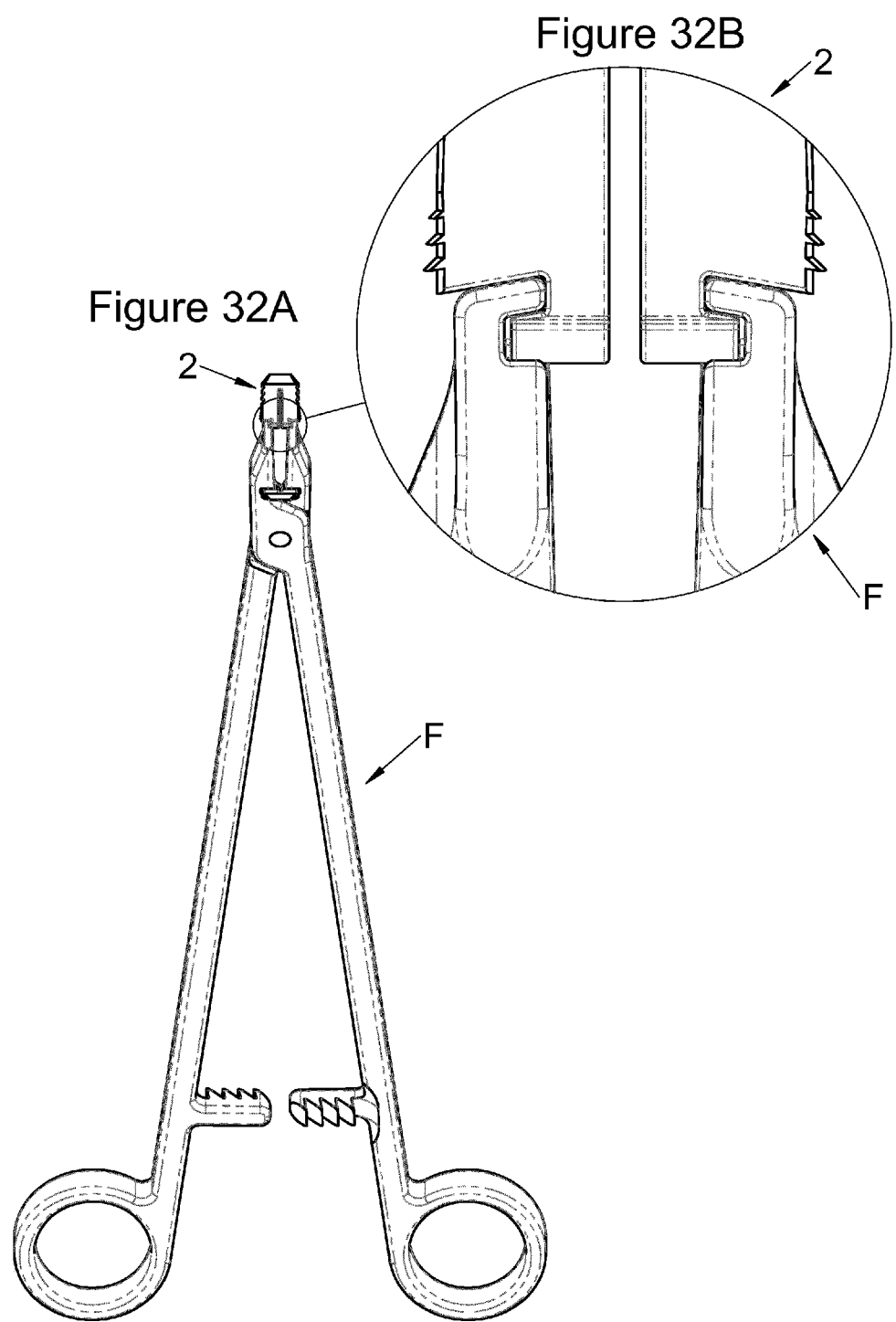

VERTEBRAL IMPLANT, VERTEBRAL FASTENING DEVICE OF THE IMPLANT AND IMPLANT INSTRUMENTATION This application is a National Stage entry of International Application PCT/EP2014/060135 filed May 16, 2014, which claims priority under 35 U.S.C. § 365(b) and 119(a) to French patent application number FR 13/54421 filed in France on May 16, 2013, each of which is incorporated herein by reference.

TECHNICAL FIELD OF THE INVENTION

This disclosure relates to the field of vertebral implants, in particular to corpectomy cages or intersomatic cages, designed to replace a vertebral segment, that is, all or part of at least one vertebral body and/or of at least one intervertebral disc. The disclosure relates more particularly to a vertebral implant, in particular to corpectomy, at least one vertebral fastening device of such an implant and implant instrumentation.

TECHNOLOGICAL BACKGROUND OF THE INVENTION

A problem in the field of vertebral implants and especially of corpectomy cages relates to deployment of an implant capable of replacing a vertebral segment, sometimes large in size, at least in height, for a corpectomy cage, since the vertebral segment can correspond to any or part of at least one vertebral body and/or at least one intervertebral disc. In fact, some pathologies, especially cancer conditions, result in degradation of vertebral bodies (in part or in totality) and/or of intervertebral discs. It is necessary to replace damaged vertebral segment(s) by an implant of considerable height. Also, it is often preferable to be able to modulate the height of the implant during surgery, since ablation of the damaged structures generally needs distraction of vertebrae to restore a physiological height (or less pathological) on the treated vertebral segment and this height varies as a function of the extent of lesions (to insert the implant between healthy tissues).

A problem associated with the problem of height of implants relates to the stabilization of the implant against the vertebral structures between which it is inserted. The necessary distraction is often incompatible with numerous stabilization solutions, such as notches on the contact surfaces of the implant, since these notches require additional distraction for insertion of the implant to be made. Also, anchoring the implant is generally preferable to simple notches that generally only limit the risks of movement but guarantee no reliable immobilization.

Solutions are known from prior art, especially for corpectomy, such as expansible cages in situ, generally comprising a body including mobile elements providing the vertebral contact surfaces and boosting the height of the implant once the latter is inserted between the vertebrae. These solutions have disadvantages of being based on generally complex and expensive mechanisms which often embrittle the implant and/or the vertebrae, since the distraction achieved by the implant during its expansion often does not test the effort exerted (such that implants sag sometimes in the vertebrae). Also, they often offer reduced graft space, disallowing the addition of a bone graft or adequate substitute. Also, these solutions have a low expansion ratio (1/3) and therefore generally require that the compressed implant be of a size already big enough so that its size is satisfactory when it is expanded and the design of these cages often means relaxing the distraction to allow their insertion into the vertebral segment. Finally, these types of expansible cages are often incompatible with notches or teeth for stabilization (as the latter reduce the capacity of real distraction, impair positioning and risk embrittling adjacent vertebral structures) and/or with anchoring (as the cages generally do not offer a sufficiently wide structure to retain anchoring means). Also, anchoring via screws can prove fastidious to be put in place and need an excessively invasive approach.

A final problem, often linked to disadvantages of solutions from prior art, relates to ablation of the implant which is generally impossible or difficult.

In this context, it is interesting to propose various embodiments for an implant that may be easily implantable, robust and reliable, adaptable to different sizes, limiting risks of embrittling adjacent vertebral structures, offers easy ablation and anchoring in the vertebral bodies without compromising final positioning and without the need for distraction superior to that required for insertion of the implant.

GENERAL DESCRIPTION OF THE INVENTION

Various embodiments of this disclosure are configured to eliminate or reduce at least one of the disadvantages of prior art disclosed hereinabove or in the art itself by proposing a vertebral implant, particularly corpectomy, which is easy to implant and fix reliably to vertebral structures adjacent to the replaced vertebral segment.

This aim is attained by a vertebral implant, for example for corpectomy, comprising at least one body of dimensions adapted to replace at least one vertebral segment, the implant comprising a peripheral wall and extending according to a vertical axis between upper and lower surfaces of the implant each designed to be placed in contact with a vertebral structure, respectively, at the top and the bottom of the vertebral segment replaced by the implant, and comprising fastening means whereof deployment enables anchoring of the implant in said lower and upper vertebral structures, each of said fastening means being deployed by sliding parallel to the vertical axis of the implant and comprising, on the one hand, at least one plate whereof at least one part remains in contact with the peripheral wall of the implant on completion of deployment and, on the other hand, at least one pointed end projecting from one of the upper and lower surfaces of the implant to enter one of said vertebral structures on completion of deployment.

This aim is also attained by a vertebral implant, in particular for corpectomy, comprising at least one body having dimensions adapted to replace at least one vertebral segment, the implant comprising a peripheral wall and extending according to a vertical axis between upper and lower surfaces of the implant each designed to be placed in contact with a vertebral structure, respectively, at the top and the bottom of the vertebral segment replaced by the implant, further comprising fastening means whereof deployment enables anchoring of the implant in said lower and upper vertebral structures, each of said fastening means being deployed by sliding inside the implant, according to a curvilinear trajectory, through a passage between the exterior of the peripheral wall and one of the upper or lower surfaces of the implant, and comprising, on the one hand, at least one curved plate whereof at least one posterior part remains inside the passage on completion of deployment and, on the other hand, at least one pointed end projecting from one of the upper and lower surfaces of the implant to enter one of said vertebral structures on completion of deployment.

Also, one of the aims of some of the embodiments is to propose a reliable and easy-to-use fastening device.

This aim may be attained by a vertebral fastening device for vertebral implant, designed to be inserted, from the periphery of the spine, through a passage between the exterior of a peripheral wall of the implant and one of the upper or lower surfaces of the implant in contact with a vertebral structure, the device comprising a body comprising at least one curved plate, rigid and elongated according to a longitudinal axis extending between an anterior end and a posterior end, the plate being configured so that its anterior end enters a vertebral structure by way of at least one pointed end while its posterior end remains in the passage of the implant, the with the plate being on the one hand curved in the plane of the plate and having a convex lateral edge, a concave lateral edge and two generally plane faces and, on the other hand, being fitted with a plurality of notches arranged to engage themselves in the wall of the passage of the implant and immobilize the fastening device in the implant when said pointed end enters said vertebral structure.

Other particular features and advantages of the various embodiments of this disclosure are detailed in the following description.

BRIEF DESCRIPTION OF THE SEVERAL VIEWS OF THE DRAWING

Other particular features and advantages of various embodiments of the disclosure will emerge more clearly from the description hereinbelow, given in reference to the attached drawings, in which:

FIGS. 15B and 15C, show, respectively, a profile view and a perspective view of the fastening means according to these embodiments, FIGS. 17A and 17B show perspective views, respectively, of an implant fitted with fastening means and fastening means alone, FIG. 17C shows a profile view of these fastening means according to some embodiments, and FIGS. 17D and 17E show, respectively, a plan view and a perspective view of fastening means according to other embodiments, FIG. 32A shows a plan view of fixing means of FIGS. 31B, 31C and 31D, held by ablation pliers, FIG. 32B is an enlargement of the part 32B designated by the circle of FIG. 32A.

DETAILED DESCRIPTION OF VARIOUS EMBODIMENTS

Figure 1A:
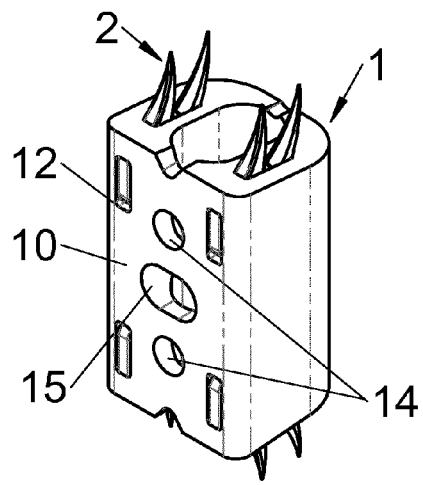
FIG. 1A shows a perspective view of an implant fitted with fastening means according to some embodiments.
Figure 1B:
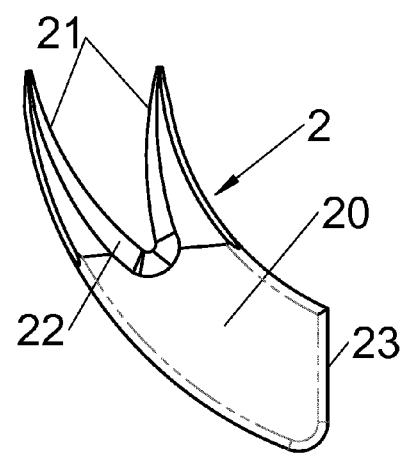
FIGS. 1B, 1C and 1D show, respectively, a profile view, a frontal view and a perspective view of the fastening means of FIG. 1A, FIGS. 2A and 2B show, respectively, a frontal view and a perspective view of an implant fitted with fastening means according to some embodiments.
Figure 1C:
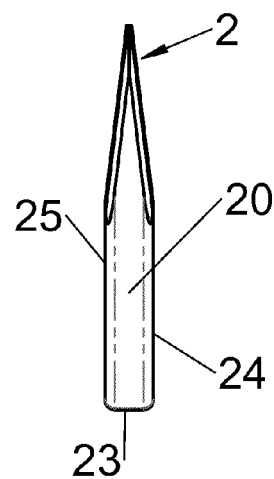
Figure 1D:
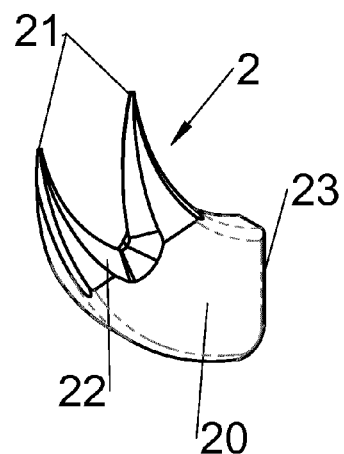
Figure 2A:
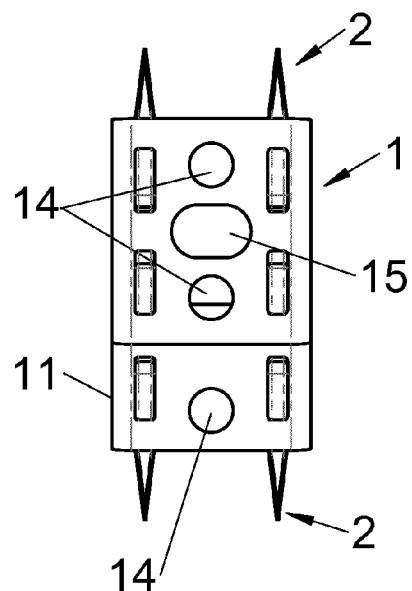
FIGS. 2C and 2D show perspective views of this same implant, respectively, before assembly with a modular body and alone (without modular body)
Figure 2B:
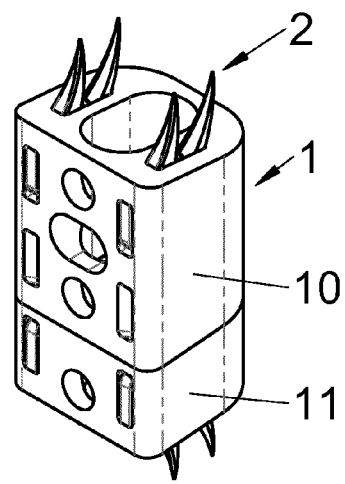
Figure 2C:
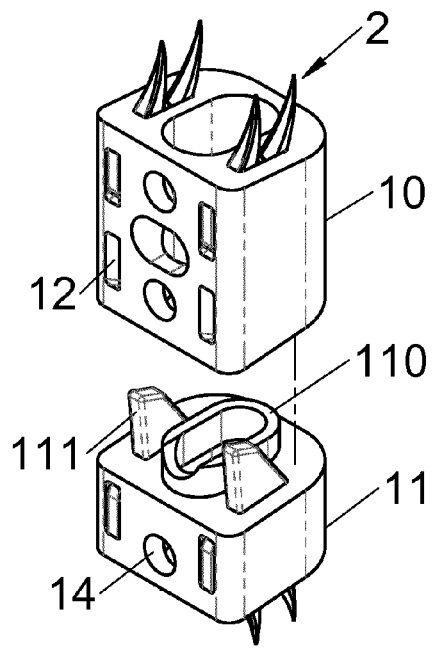
Figure 2D:
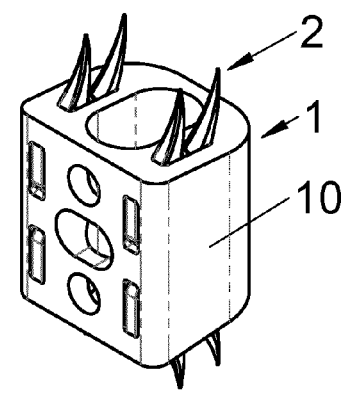

This disclosure relates to vertebral implants, especially for performing a corpectomy, that is, ablation of a vertebral segment and insertion of an implant replacing the removed tissue. This disclosure also relates to at least one fastening device of implants in general, and especially (though not only) of the type specified in the present application. These fixing devices are also designated in the present application by the terms "anchor" or "anchoring" or even "fastening means". This disclosure also relates to implant instrumentation for insertion of an implant (which may include the types described in the present application) and instrumentation for fixing implants by a fastening device such as those disclosed in the present application. The term "vertebral segment" is used in the present description in its accepted form signifying "a part of the spine" since it can correspond to all or part of at least one vertebral body and/or of at least one intervertebral disc. In fact, corpectomy can relate to at least one whole vertebral body, or even an entire vertebra and its adjacent intervertebral discs but can relate also to only part of a vertebral body or several vertebral bodies, in all or part, and at least one part of at least one of the adjacent intervertebral discs. For example, especially in the case of a cancerous condition, a vertebral body can be touched only partially and advantage can be taken by preserving the healthy part to accommodate an implant. So, various embodiments of the present description are configured to fix the implant in a "vertebral structure" and this term is used in the present description in its accepted form signifying "at least one part of at least one element constituting the spine" since it can correspond to all or part of at least one vertebral body and/or of at least one intervertebral disc. The terms specified hereinabove and all the terms used in the present description must therefore not be interpreted as limiting, and the present application makes it clear that it is generally a functional definition that is given to the elements and characteristics described. For example, the term "vertebral implant" is used to designate the fact that the implant can relate to a vertebral segment, that is, at least one vertebral body and/at least or an intervertebral disc. The implant can therefore correspond to a corpectomy cage but also to an intersomatic cage, for example. Also, vertebral fixing devices, for fixing in a "vertebral structure", can be used to fix various types of vertebral implants, especially corpectomy cages, intersomatic cages, disc prostheses or osteosynthesis plates, etc.

The implants of some embodiments are preferably made of PEEK (polyetheretherketone) which has physical properties, especially rigidity, close to those of osseous tissues, and which improves post-operative radiology follow-up (as opposed to implants made of titanium or other metal or alloy which may create MRI flashing, aggravated by the fact that implants used for arthrodesis are often accompanied by osteosynthesis plates). Fixing devices, however, are preferably made of metal or biocompatible alloy such as titanium, to ensure substantial resistance, but other materials are possible.

With respect to implantation, various methods of approach for placing the implant are possible, even if a given method for each of the various spinal stages is generally preferred. An anterior median mini-invasive approach (MIS, for Mini-Invasive Spine Surgery) for cervical vertebrae and a lateral or antero-lateral mini-invasive approach for thoracic or lumbar vertebrae could be preferred, for example (non-limiting).

Preferably, in the case of intersomatic cages or corpectomy in particular, the implant is hollow, by way of at least one opening extending from said upper surface as far as said lower surface, as is visible particularly on the majority of the figures non-limitingly illustrating corpectomy cages. Such an opening of the implant between its surfaces in contact with vertebral structures adjacent to the replaced vertebral segment enable insertion of cement and/or an osseous growth inside the implant (1) and offers a wide space of continuous graft for adding the bone graft or the substitute to consolidate the vertebral segment operated on. The insertion of cement can also lock the various bodies making up the implant. Therefore, in some embodiments, as shown in the majority of the figures, the peripheral wall comprises at least one conduit (15) to allow insertion of a graft and/or osseous substitute in the implant for easier osseous growth through the opening of the implant. Also, it is provided in general that the different elements of the implant and fastening means also offer such an opening. For example, in the embodiment of FIG. 21, the fastening means plate (52) is fitted with at least one hole (53) ensuring continuity of the opening of the implant (1) as far as the vertebral structures.

In general, some embodiments preferably comprise at least one vertebral implant (1), in particular corpectomy, comprising at least one body (10, 11, 3, 3m, 3f) having dimensions adapted to replace at least one vertebral segment. This implant (1) generally comprises a peripheral wall and extends according to a vertical axis between the upper and lower surfaces of the implant (1) which are each designed to be placed in contact with a vertebral structure, respectively, at the top and the bottom of the vertebral segment replaced by the implant (1). The peripheral wall preferably comprises hooking means (14, 34) for implant instrumentation. By way of advantage, the implant (1) comprises or is associated with fastening means (2, 2a, 5, 8) the deployment of which enables anchoring of the implant in said lower and upper vertebral structures. To eliminate at least one of the disadvantages of the prior art, each of said fastening means (2, 2a, 5, 8) is deployed by sliding along at least one part of the implant (1). In various embodiments, these fastening means (2, 2a, 5, 8) are deployed by sliding inside the implant or about the periphery of the implant. Also, in various embodiments detailed hereinbelow and which exhibit their respective advantages, these fastening means (2, 2a, 5, 8) slide according to a rectilinear trajectory parallel to the vertical axis (which in turn is generally parallel to the axis of the spine when the implant is placed in the treated vertebral segment) or according to a curvilinear trajectory, preferably through a passage (12) between the exterior of the peripheral wall and one of the upper or lower surfaces of the implant (1). Finally, as detailed hereinbelow in various advantageous embodiments, these fastening means (2, 2a, 5, 8) preferably comprise at least one plate (20, 52, 82,) whereof at least one part remains in contact with the implant (1) on completion of deployment to ensure proper fixing stability. Also, as detailed hereinbelow in various advantageous embodiments, these fastening means (2, 2a, 5, 8) generally comprise at least one pointed end (21, 51, 81) projecting from one of the upper and lower surfaces of the implant (1) to enter one of said vertebral structures on completion of deployment. Preferably, several pointed ends are provided to ensure better stability by way of several fixing points. Finally, in some embodiments, those parts of the fastening means which penetrate the vertebral structures preferably comprise portions of plates whereof the width provides resistance to movement (of the patient which possibly have an impact on the implant) enabling good stability in the spine (better than that allowed by portions of less substantial extent, such as points or staples). In general at least one fixing means (2, 2a, 5, 8) for each of the upper and lower vertebral structures on the treated vertebral segment is provided, as shown in the majority of the figures, but it is possible to fix the implant only on one of these vertebral structures. Also, it is clear that fastening means can be provided according to embodiments of the present application that may be different for these two vertebral structures or even at least one fixing means different from those of the present application. It is evident that the fastening means are generally rigid, for example made of metal or alloy to provided good stability, even if the possibility of flexion of a portion of the anchor is provided in some embodiments (in this case, it is the particular arrangement which allows restricted flexion and not the material).

Implants

The implant comprises at least one body (10, 11, 3, 3m, 3f) having dimensions adapted to replace the treated vertebral segment. The general form of the implant can vary as a function of various configurations and it is not necessary to detail it as such, with the exception that it defines a vertical axis (designated here as parallel to the axis of the spine for greater simplicity). Also, the body could have a form for imposing or correcting lordosis by way of the non-parallel upper and lower surfaces.

In some embodiments, the implant (1) comprises several bodies (10, 11, 3, 3m, 3f) complementary to each other and stackable along the vertical axis to adapt the height of the implant (1) to the size of the vertebral segment to be replaced; this also minimizes the number of implants necessary to cover the whole range of possible height. These bodies can generally be nested together, or even locked to ensure proper cohesion of the assembly. These bodies can also comprise hooking means (14, 34) for instrumentation. Various forms of bolting are possible, such as dovetails, threading and tapping, spurs, or projections cooperating with complementary housings, etc., but it is not mandatory to lock the bodies together if a male-female nesting is provided over a sufficient height so that they do not separate during movement (from the patient, in particular). In fact, movements have a very small range at the vertebral level and the male and female elements, due to which two bodies fit together, only have to have dimensions (vertically) greater than this amplitude to ensure good stability of the assembly.

In some embodiments, illustrative and non-limiting examples of which are shown in FIGS. 2A to 2D, the implant (1) comprises a main body (10) useable alone or in combination with an additional body (11) complementary to at least one of the upper or lower surfaces of the main body (10), said additional body (11) comprising means (110, 111) for fitting with the main body (10) and fastening means (2, 2a, 5, 8) sliding relative to the additional body to enter one of said vertebral structures.

Figure 3A:
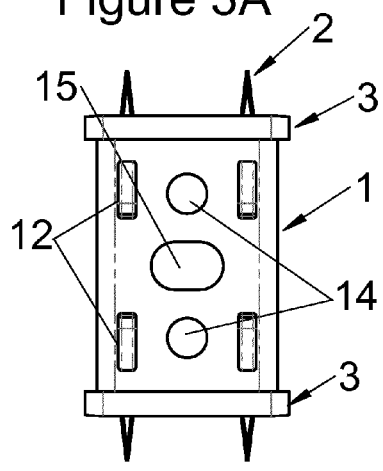
FIGS. 3A and 3B show, respectively, a frontal view and a perspective view of an implant fitted with fastening means according to some embodiments.
Figure 3B:
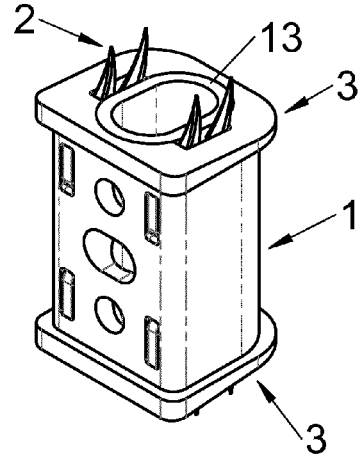
Figure 3C:
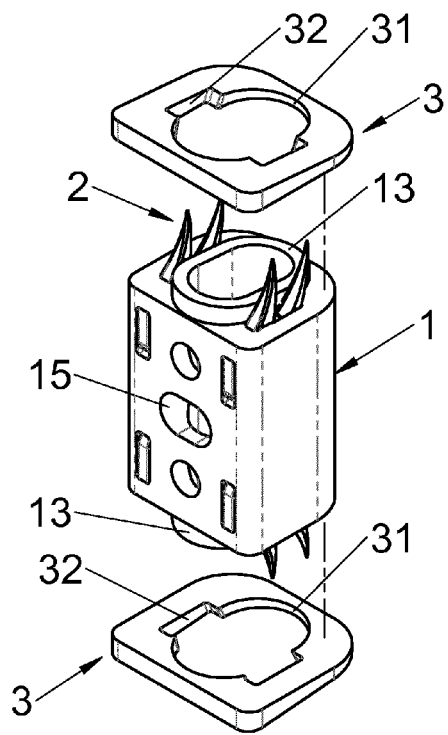
FIG. 3C shows a perspective view of this same implant before assembly with vertebral contact plates.
Figure 4A:
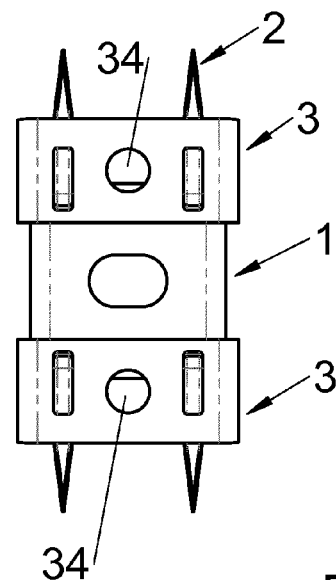
FIGS. 4A and 4B show, respectively, a frontal view and a perspective view of an implant fitted with fastening means according to some embodiments.
Figure 4B:
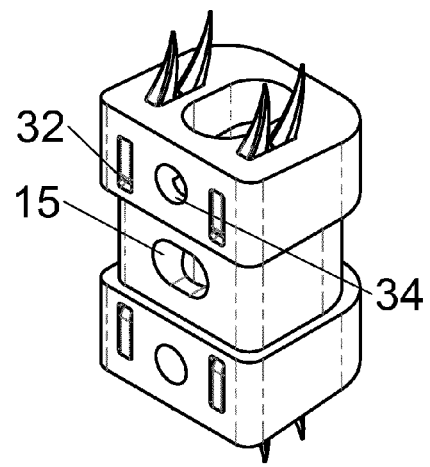
Figure 4C:
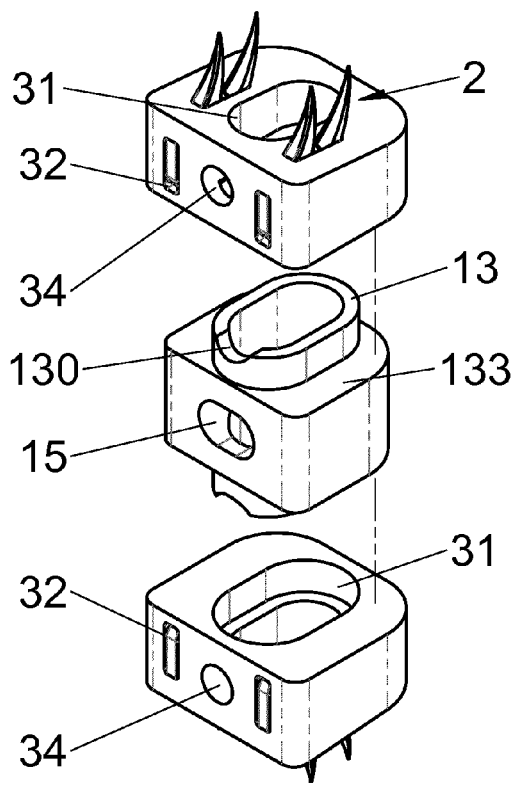
FIG. 4C shows a perspective view of this same implant before assembly with two modular bodies.
Figure 5A:
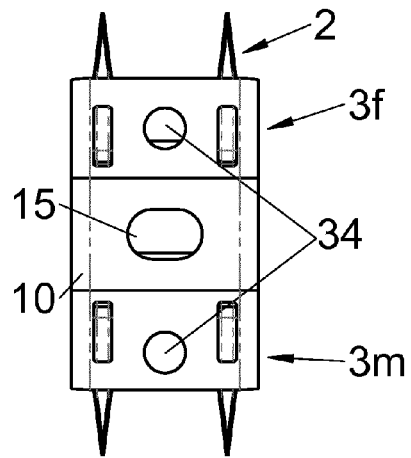
FIGS. 5A and 5B show, respectively, a frontal view and a perspective view of an implant fitted with fastening means according to some embodiments.
Figure 5B:
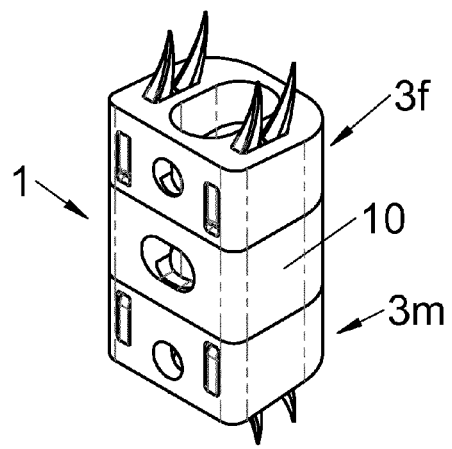
Figure 5C:
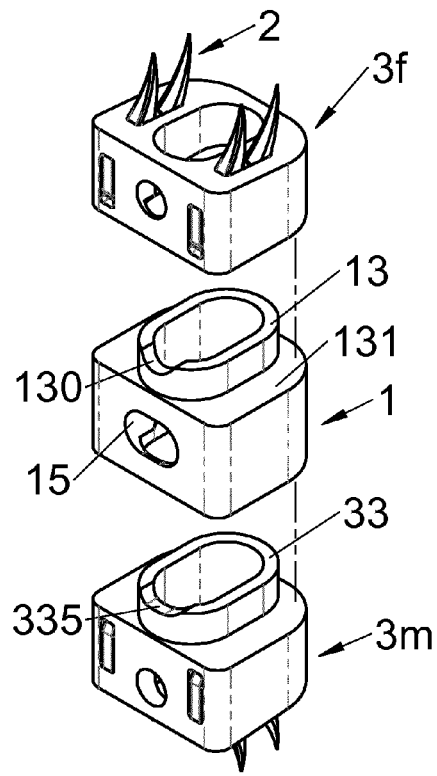
FIG. 5C shows a perspective view of this same implant before assembly with two modular bodies and FIG. 5D shows a perspective view of the two modular bodies assembled alone.
Figure 5D:
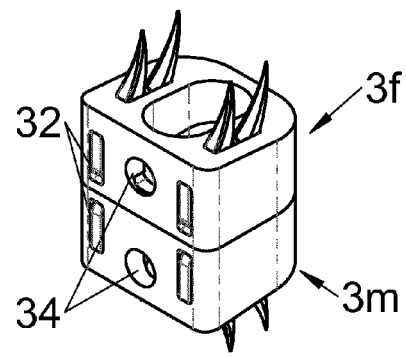
Figure 6A:
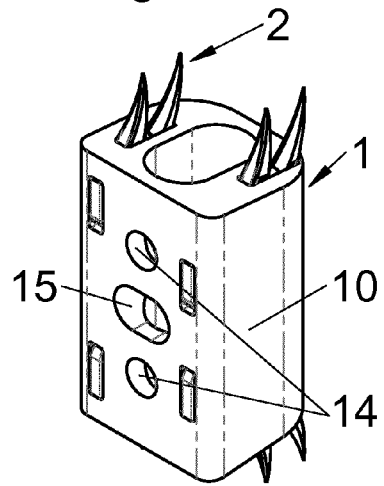
FIGS. 6A, 6B, 6C, 6D and 6E show perspective views of an implant fitted with fastening means according to different embodiments.
Figure 6B:
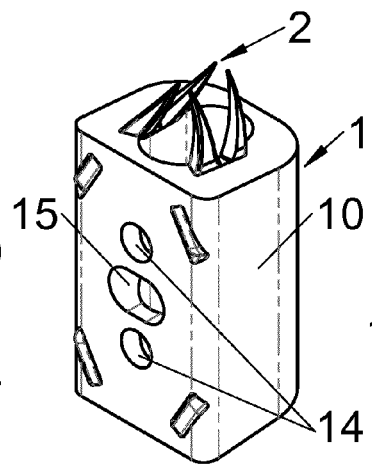
Figure 6C:
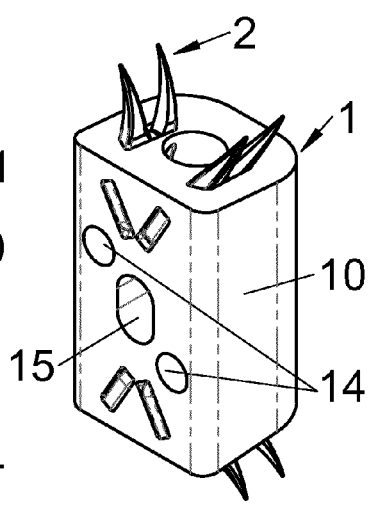
Figure 6D:
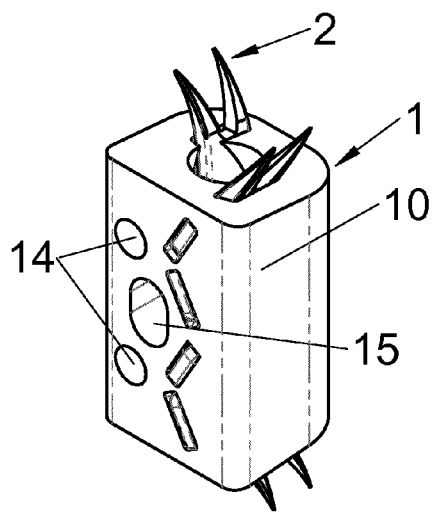
Figure 6E:
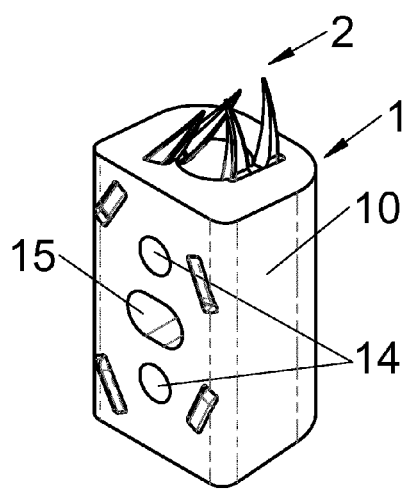
Figure 28A:
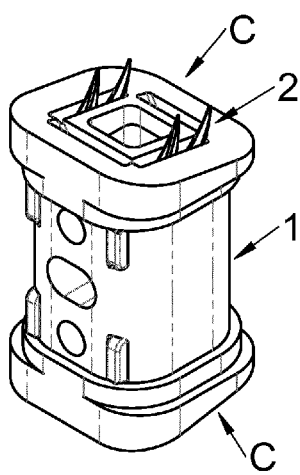
FIGS. 28A, 28B, 28C, 28D and 28E show perspective views of an implant fitted with its fastening means and vertebral contact plates according to different embodiments.
Figure 28B:
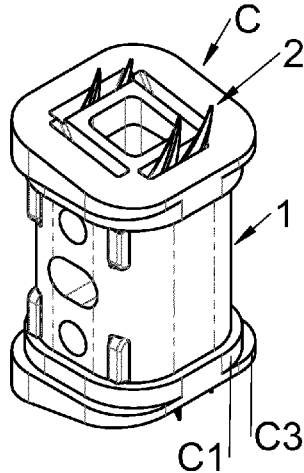
Figure 28C:
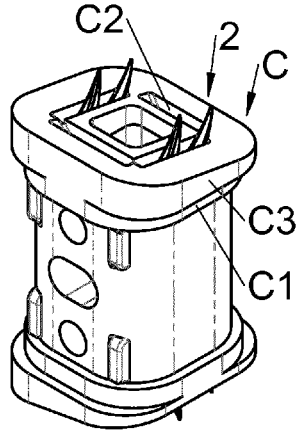
Figure 28D:
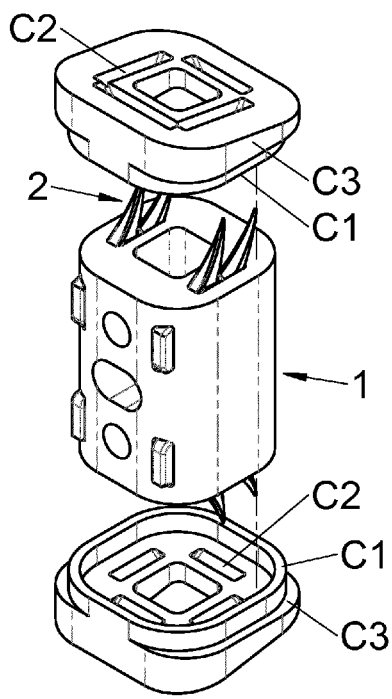
Figure 28E:
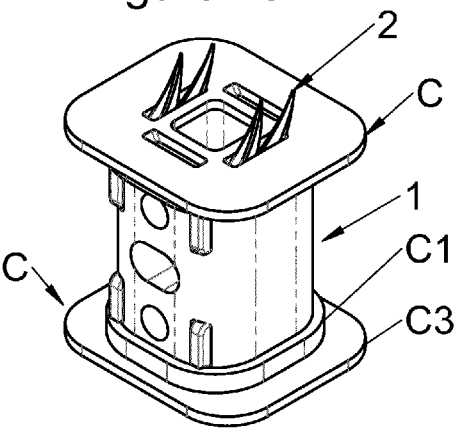

In some embodiments, illustrative and non-limiting examples of which are shown in FIGS. 3A to 3C, 4A to 4C) and 5A to 5D, the implant (1) comprises two additional bodies (3, 3m, 3f). In some of these embodiments, the additional bodies (3) form trays (plateaus or end members)

arranged on the upper and lower surfaces of the implant, for example as shown in FIGS. 3 (A to C). In these examples, the body of the implant comprises on its lower and upper surfaces fitting means (13) for taking up these trays comprising complementary fitting means (33) (the male-female configuration shown in FIG. 3C can clearly be reversed). Such trays can act as anatomical adaptation elements to take the form of vertebral structures and/or impose or correct lordosis, for example the correcting trays (C) shown in FIG. 28 (A to E). Some trays (C) also augment the vertebral contact surface, evident for example in FIG. 28E. These trays can for example comprise a plate (C3) fitted with a lip (C1) having dimensions adapted to accommodate the periphery of the implant, but fitting means of the type of those described hereinabove or hereinbelow can also be provided (similarly, the fitting means of the additional bodies can be the same type as these lips). In some embodiments of these trays (C), holes (C2) are provided for passage of fastening means such that vertebral anchoring is achieved by trays (C) which will be locked against the vertebral structures. Sufficiently long pointed ends (51, 21) can be provided optionally on the fastening means to pass through the trays even at their thickest portion. Such additional bodies (3) can comprise at least one passage (32) for the fastening means (2, 2a, 5, 8) of the implant, such as for example illustrated non-limitingly in FIG. 3C, or can comprise a structure (such as housings (32) or passages) for taking up the fastening means, for example illustrated non-limitingly in FIGS. 4 and 5. In some embodiments, for example as in FIG. 4C, the two additional bodies (3) are identical (which provides the advantage of limiting production costs) and are complementary to the main body (via the fitting means). In this way, female fitting means (31) of the additional bodies (3) for example receive male fitting means (13) of the main body (10), or vice versa. It is evident that complementary mixed (male and female) fitting means can be provided to interchangeably stack several bodies on each other. Also, in addition to the fitting means, an adequate support surface (133) is generally provided so that the bodies rest stably on each other. It is also evident that the bodies, especially on their fitting means, can comprise cutouts (130, 335) so as not to impair the function of other means of the implant, as evident for example in FIG. 4C. In some particularly advantageous embodiments for height adaptation of the implant to the size of the treated vertebral segment, additional bodies (3m, 3f) are provided, each of which can be used in combination with the main body (10) of the implant (1) and/or are complementary to each other and useable alone, in combination with each other, in the absence of a main body (10), such as for example illustrated in FIG. 5D. In such modes, as evident especially in FIG. 5C, the main body (10) comprises for example male fitting means (13) on one of its lower or upper surfaces and female fitting means on the other surface. So, an additional body (3m) with male fitting means (33) cooperates with the female fitting means of the main body (10) or the other additional body (3f) whereof the female fitting means can also cooperate with the male fitting means (13) of the main body (10). It is therefore possible to use a single additional body (3f) in combination with the main body (10) or two additional bodies (3m, 3f) together or two additional bodies (3m, 3f) in combination with the main body (10). It is evident that the main and additional bodies illustrated in FIGS. 2 to 5 illustrate the various possibilities in the case of some fastening means but it is clear that these illustrations are not limiting and that various embodiments may use different or additional bodies. In fact, the main body can be separated (or is separable) into two, between its upper and lower surfaces, particularly between the elements which receive the fastening means, thus one or more additional bodies can be nested between the two separated parts, for example by way of fitting means of the type of those shown in FIG. 5C.

Figure 29A:
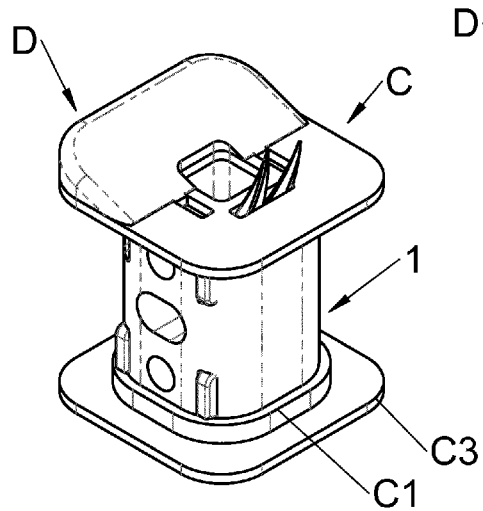
FIGS. 29A, 29B and 29C show perspective views of an implant fitted with its fastening means, vertebral contact plates and vertebral adaptation trays according to different embodiments.
Figure 29B:
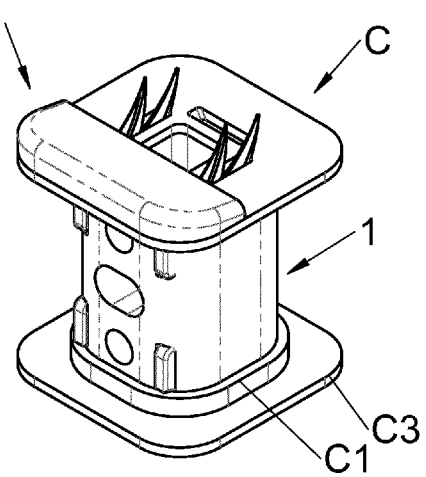
Figure 29C:
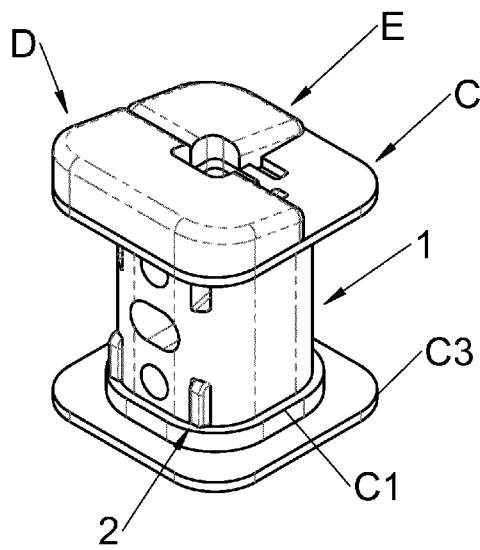

In some embodiments, particularly advantageous when the vertebral structures exhibit strong irregularities (for example because the entire vertebral body is not removed during surgery), the implant can comprise additional adaptation elements (D, E), for example as illustrated in FIG. 29 (A to C). For example, wedges (D) covering half the vertebral contact surface or wedges (E) covering quarter of the vertebral contact surface or any wedge covering any value of the contact surface can be added to the implant, directly to its lower or upper surfaces, or to adaptation or correction trays (C) (as in FIGS. 29A to C), or to the additional bodies.

Anchorings

Some embodiments, illustrative and non-limiting examples of which are shown in FIGS. 20 to 25, relate to a vertebral implant (1), in particular for corpectomy, comprising at least one body (10, 11, 3, 3m, 3f) having dimensions adapted to replace at least one vertebral segment, the implant (1) comprising a peripheral wall and extending according to a vertical axis between the upper and lower surfaces of the implant (1) each designed to be placed in contact with a vertebral structure, respectively, at the top and the bottom of the vertebral segment replaced by the implant (1). This type of implant comprises fastening means (5, 8) deployment of which enables anchoring of the implant in said lower and upper vertebral structures, each of said fastening means (5, 8) being deployed by sliding parallel to the vertical axis of the implant (1). These fastening means (5, 8) comprise, on the one hand, at least one plate (52, 82) whereof at least one part remains in contact with the implant (1) on completion of deployment and, on the other hand, at least one pointed end (51, 81) projecting from one of the upper and lower surfaces of the implant (1) to enter one of said vertebral structures on completion of deployment.

In some of these embodiments, illustrative and non-limiting examples of which are shown in FIGS. 20 and 21, the fastening means (5) slide inside the peripheral wall of the implant (1), parallel to the vertical axis. For example, in some embodiments shown in FIGS. 20 (A to D) said plate (52) of the fastening means (5) is arranged, inside the implant, in a plane perpendicular to the vertical axis and is fitted with at least one point (51) oriented according to the vertical axis. This type of anchoring is for example inserted in the implant (1), perpendicularly to the vertical axis, via at least one housing (56) in the peripheral wall of the implant (1), said housing (56) having a width complementary to the width of the plate (52) and a height at least equal to that of the fastening means (5). This housing (56) terminates at one of the lower or upper surfaces of the implant (1) via at least one hole receiving said point (51) such that the latter penetrates one of said vertebral structures through this hole in the lower or upper surface. In general, several points (51) are provided, four points for example as shown in FIGS. 20 (A, B and D). The plate (52) has a generally rectangular form for example on which the points (51) are arranged, perpendicularly to the plane of the plate (52). The plate is guided in vertical translation inside the housing (56) during deployment. At least one fixing means (5) is provided in general for each of the upper and lower vertebral structures on the treated vertebral segment. This deployment can be carried out, as shown for example by way of illustration in FIG.

20B, by means of a spacer (6) whereof the branches (65) are each inserted into one of the two upper and lower housings (56) of the implant (1) to push on the two fastening means at the same time. This deployment can also be carried out, as shown for example by way of illustration in FIGS. 20C and 20D, by means of at least one stylus (7) whereof an end (75) tapers progressively, such that when it is inserted further into the housing (56), it pushes the plate (52) in the direction of the vertebral structure towards which the pointed end (51) of the fastening means (5) points. This type of use of the spacer (6) and of the stylus (7) is the same for numerous embodiments of the fastening means and it will not be detailed again for the other modes, since it is clear that those of ordinary skills in the art will appreciate the operation and the use of these tools or instruments in the various embodiments described in the present application. In another example, especially such as some embodiments shown in FIGS. 21 (A to D), said plate (52) of the fastening means (5) is arranged in a plane perpendicular to the vertical axis, fitted with at least one point (51) oriented according to the vertical axis and inserted in the implant (1), parallel to the vertical axis, via at least one housing in one of the upper and lower surfaces of the implant (1). The periphery of said plate (52) remains in contact with the walls of this housing when said point (51) enters one of said vertebral structures to stabilize the assembly, the plate (52) and the housing of the implant (1) having complementary shapes, as evident especially in FIG. 21A. It is evident that the forms illustrated are illustrative and that various forms can be selected, of course. The plate (52) preferably comprises a hole (53) providing continuity with the opening passing through the implant for osseous growth, if need be. Fasteners or locks may be provided so as to avoid any movements of the fixation/fastening means (5) when deployed. Such fasteners or locks may comprise various mechanisms such as snap-fit studs, sliding pins, tenon and mortise, etc.

In some embodiments, illustrative and non-limiting examples of which are shown in FIGS. 22 to 25, the fastening means (5, 8) slide around the peripheral wall of the implant (1), parallel to the vertical axis. For example, said plate (52, 82) of the fastening means (5, 8) comprises at least one hole (53) having dimensions at least equal to those of the periphery of the implant (1) and forming a crown arranged in a plane perpendicular to the vertical axis and sliding around the peripheral wall the implant (1), parallel to this vertical axis. Blocking means (16, 17, 18, 54) limiting the sliding of said plate (52, 82) are generally provided so that the plate (52, 82) remains in contact with the peripheral wall of the implant (1) when said pointed end (51, 81) penetrates one of said vertebral structures. In some of these embodiments, illustrative and non-limiting examples of which are shown in FIGS. 22 (A to D), 23 (A to D) and 30 (C and D), said blocking means (16, 17, 54) limiting the sliding of said plate (52) comprise, on the one hand, a groove (54) in the wall of the hole (53) of said plate (52) and a groove (16) in the peripheral wall, in the region of at least one of the lower and upper surfaces of the implant (1), and, on the other hand, a slotted ring (17) which fits into the two grooves (16, 54), similarly to a clamping clip, to block the plate (52) relative to the implant (1) when said pointed end (51) penetrates one of said vertebral structures. It is evident that the slotted ring can comprise fingers or eyelets to make its placement on the groove (16) of the implant easier. An access housing (54) to the ring, especially its fingers or eyelets, can also be provided in the plate (52) to facilitate ablation. In other embodiments, illustrative and non-limiting examples of which are shown in FIGS. 24 (A to E), 25 (A to D) and 30 (A and B), said blocking means (18) limiting the sliding of said plate (52, 82) comprise a crown (18) mounted in the region of at least one of the lower and upper surfaces of the implant (1) to block the plate (52, 82) relative to the implant (1) when said pointed end (51, 81) penetrates one of said vertebral structures through at least one hole (195, 188) in said crown (18).

Figure 25A:
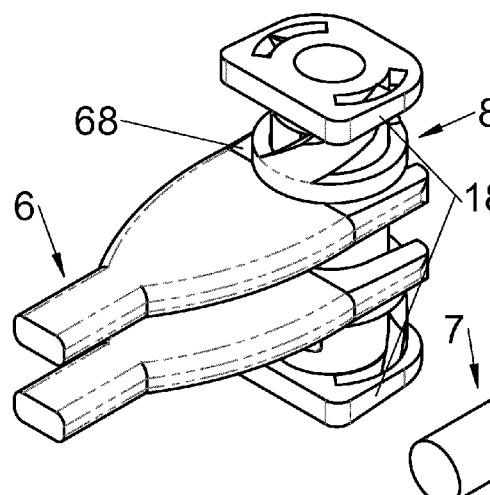
FIG. 25D shows the fastening means alone of the embodiments of FIG. 25C, FIGS. 26A and 26E show perspective views of an implant according to some embodiments and a spacer for insertion of these implants.
Figure 25B:
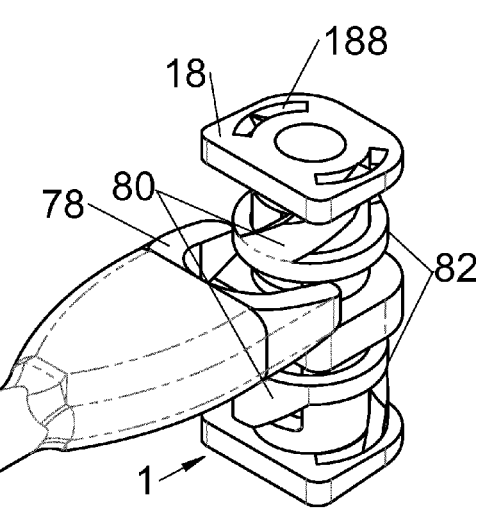
Figure 25C:
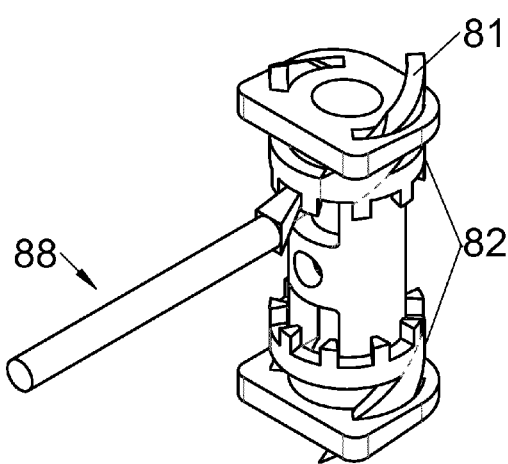
Figure 25D:
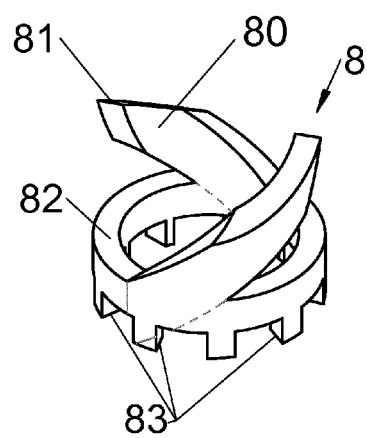

In some embodiments, illustrative and non-limiting examples of which are shown in FIGS. 22 (A to D), 23 (A to D) and 30 (A to D), said plate (52) which slides about the implant is fitted with at least one straight and vertical point (51) forming said pointed end penetrating one of said vertebral structures. In other embodiments, illustrative and non-limiting examples of which are shown in FIGS. 24 (A to E) and 25 (A to D), the sliding plate (82) is fitted with at least one helicoidal plate (80) fitted with at least one point (81), forming said pointed end penetrating one of said vertebral structures via vertical sliding accompanied by rotation, according to a helicoidal movement. The helicoidal plate (80) fitted with at least one point (81) is often designated hereinbelow by the term "helicoidal point (81)" for simplicity but it is clear that this is preferably a pointed plate even though it can simply be a pointed rod. In some of these embodiments, deployment of the fastening means (5, 8) can be carried out by means of a spacer (6) as described previously, preferably a spacer (6) with double branches whereof both branches (66, 68) pass on either side of the peripheral wall, for example as in FIG. 23C, 23D or 25A. In some of these embodiments, deployment of the fastening means (5, 8) can be carried out by means of a stylus (7) as described previously, preferably a stylus (7) with double branches whereof both branches (76, 78) pass on either side of the peripheral wall and are supported for example to push said sliding plate (52, 82), on a bead (19) projecting on the periphery of the peripheral wall between the upper and lower surfaces (for example halfway), for example as in FIG. 22C, 22D or 25B. It is evident that such a bead can in fact be an additional body interposed between two portions bearing the fastening means, similarly to the explanation supplied earlier in the present application. In some embodiments, illustrative and non-limiting examples of which are shown in FIGS. 25C and 25D, the sliding plate (82) with helicoidal points (81) comprises, on its face opposite that fitted with the points, notches, teeth or crenellations (83) configured so that a tool (88) comprising an end of form complementary to these notches (83) can be used to anchor the helicoidal points in the vertebral structures. In fact, in the case of an osseous structure, it is often necessary to proceed by "impingement", that is, by striking on a tool transmitting the shocks to the fastening means. In this way, by successively using the various notches (83) of the plate (82) it is possible to aid translation and especially rotation of the plate, necessary for penetration of the helicoidal points in the vertebral structures.

It is evident in the embodiments described hereinabove that the points (51, 81), even if they are often illustrated by a sharpened cylindrical element (resembling a nail), are preferably formed by sharpened plates which offer better stability in the bone. Preferably, when several points (51, 81) in the form of a plate are used for the same vertebral structure, the plane of these plates will be oriented not parallel relative to each other (for example perpendicularly) such that the vertebral fixing is opposed optimally to movements in several directions.

It is also evident that various embodiments allow the fastening means to be pre-mounted on the implants for easier preparation of implantation during surgery.

Figure 7A:
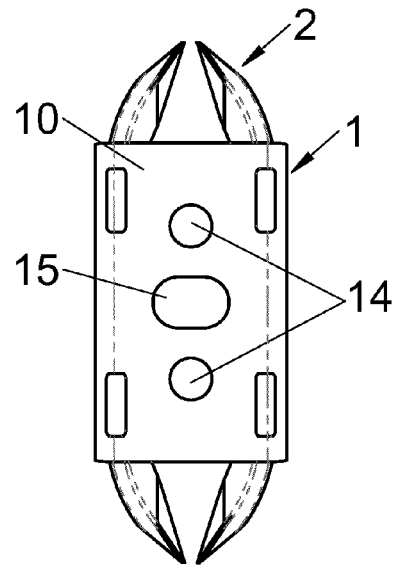
FIGS. 7A and 7C show, respectively, a frontal view and a perspective view of an implant fitted with fastening means according to some embodiments.
Figure 7B:
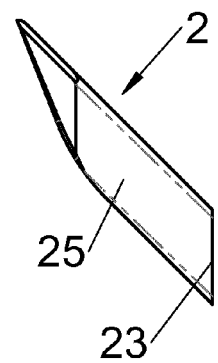
FIGS. 7B and 7E show, respectively, a profile view and a perspective view of the fastening means of the implants in FIGS. 7A and 7C or FIGS. 7D and 7F, FIGS. 8A and 8B show sectional views on the one hand of an implant, respectively, after and before insertion of fastening means according to some embodiments.
Figure 7C:
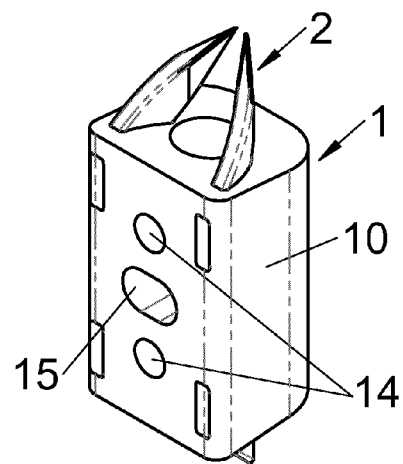
Figure 7D:
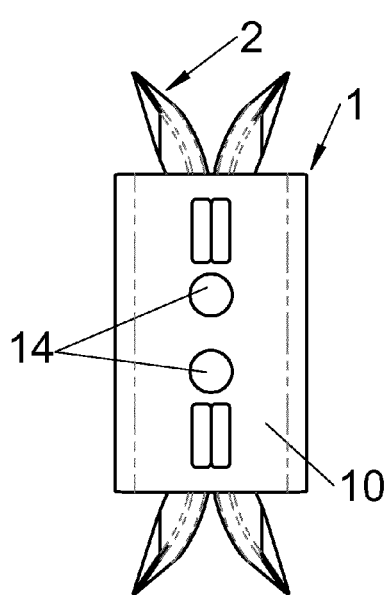
FIGS. 7D and 7F show, respectively, a frontal view and a perspective view of an implant fitted with fastening means according to other embodiments
Figure 7E:
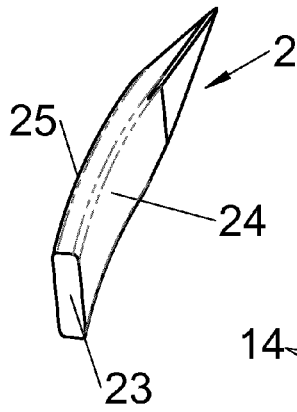
Figure 7F:
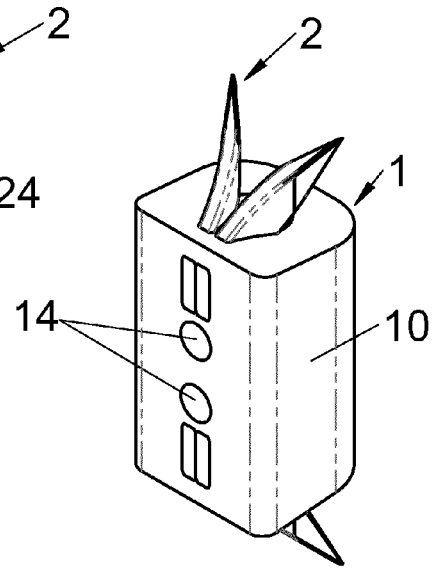

As detailed earlier in the present application, some embodiments relate to fastening means inserted according to a curvilinear trajectory and/or an implant comprising such fastening means. Such a trajectory is advantageous since it anchors the implant by using the same method of approach as that used for insertion of the implant in the treated vertebral segment and therefore allows easier access for impingement of fastening means in the vertebrae, especially according to an approach axis perpendicular to the axis of the spine (at least approximately). So, some embodiments relate to a vertebral implant (1), in particular for corpectomy, comprising at least one body (10, 11, 3, 3m, 3f) having dimensions adapted to replace at least one vertebral segment, the implant (1) comprising a peripheral wall and extending according to a vertical axis between the upper and lower surfaces of the implant (1), each designed to be placed in contact with a vertebral structure, respectively, at the top and the bottom of the vertebral segment replaced by the implant (1). This implant comprises fastening means (2, 2a, 2d) deployment of which enables anchoring of the implant in said lower and upper vertebral structures, each of said fastening means (2, 2a, 2d) being deployed by sliding inside the implant (1), according to a curvilinear trajectory, via a conduit or passage (12) between the exterior of the peripheral wall and one of the upper or lower surfaces of the implant (1). These fastening means (2, 2a, 2d) comprise, on the one hand, at least one curved plate (20) whereof at least one posterior part remains inside the passage (12) on completion of deployment and, on the other hand, at least one pointed end (21) projecting from one of the upper and lower surfaces of the implant (1) to enter one of said vertebral structures on completion of deployment. This curved plate (20) is preferably curved in the plane defined by the plate and therefore generally has a convex lateral edge, a concave lateral edge and two generally plane faces, as is generally visible in the majority of figures. All the same, in some embodiments, illustrative and non-limiting examples of which are shown in FIGS. 17, 18 and 19, the curve of the plate is not in the plane defined by the plate since it does not define a plane, but in contrast, the plate is arched and therefore has a concave face, a convex face and two straight lateral edges. Also, in some embodiments, illustrative and non-limiting examples of which are shown in FIGS. 7B and 7E, the plate is curved in both directions at the same time and therefore has a concave edge, a concave face (24), a convex edge and a convex face (25). This double curve orients the anchoring in various directions as needed, as can be seen particularly in FIGS. 7A and 7C or in FIGS. 7D and 7F.

In these embodiments, the implant is therefore linked to fastening means which are used after insertion of the implant, as opposed to the embodiments described hereinabove. Such fastening means forming an arched plate only need for the implant to have one passage (12) such as described. In this way, this disclosure also relates to just the fastening device. In some embodiments, this disclosure therefore relates to a vertebral fixing device (2, 2a, 2d) for vertebral implant (1), designed to be inserted, from the periphery of the spine, through a conduit or passage (12) between the exterior of a peripheral wall of the implant and one of the upper or lower surfaces of the implant (1) in contact with a vertebral structure, the device (2, 2a, 2d) comprising a body comprising at least one curved plate (20), rigid and elongated according to a longitudinal axis extending between an anterior end and a posterior end (23, 23a, 23d), the plate (20) being configured so that its anterior end enters a vertebral structure by way of at least one pointed end (21) while its posterior end (23, 23a, 23d) remains in the passage (12) of the implant (1). This fixing device (2, 2a, 2d) is preferably configured with a plate (20) which is curved in the plane of the plate and has a convex lateral edge, a concave lateral edge and two generally plane faces. Also, the plate (20) of this device (2, 2a, 2d) is preferably fitted with a plurality of notches (27) arranged to fit in the wall of the passage (12) of the implant (1) and immobilize the fastening device (2, 2a, 2d) in the implant (1) when said pointed end enters said vertebral structure.

Figure 8A:
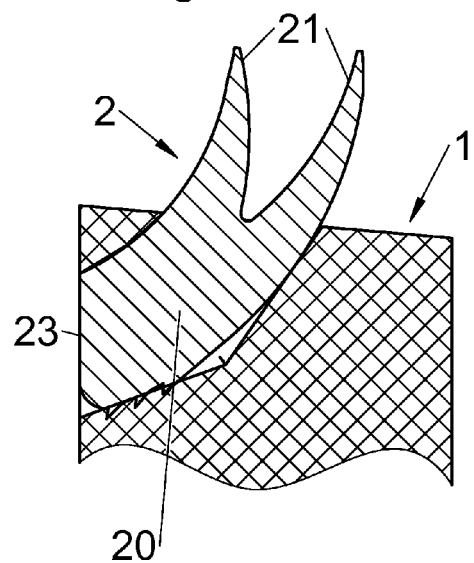
FIGS. 8C and 8D show sectional views on the other hand of an implant, respectively, after and before insertion of fastening means according to other embodiments.
Figure 8B:
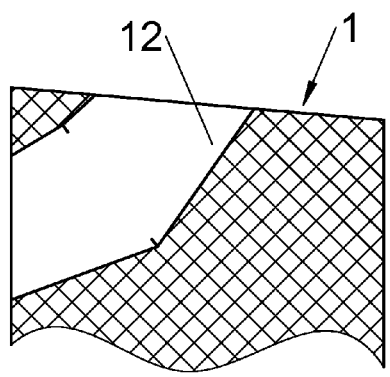
Figure 8C:
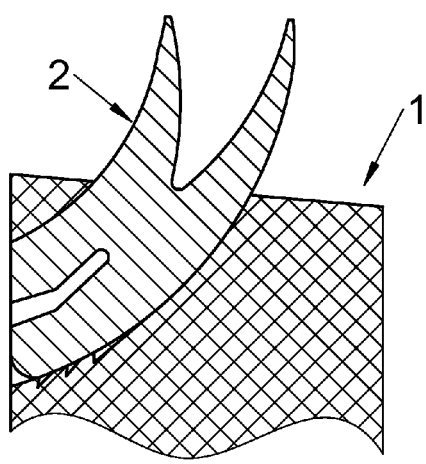
Figure 8D:
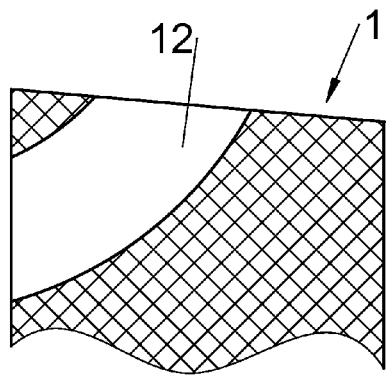

The embodiments described hereinbelow also refer to the implant comprising the anchor in the form of a curved plate as the anchor itself, hereinbelow sometimes designated by the term "arched plate". A posterior part of the arched plate remains in the implant and this part must be adequate to fit well in the implant. The posterior end (23, 23a, 23d) is preferably in the implant also, flush with the entry of the passage or at least without exceeding the peripheral wall too much, which would risk damaging surrounding tissues. In some embodiments, said curved plate (20) is arranged in a vertical plane inside the passage (12) of the implant (1) and the curve of the plate (20) is oriented in this vertical plane. The passage therefore has a generally rectangular section (optionally with rounded edges) with a width at least equal to the thickness of the arched plate (20) and a length (or height since it is vertical) at least approximately equal to the width of the arched plate (20). The arched plate has an approximately constant width over its entire posterior portion designed to remain in the implant but can be slightly wider at its posterior end to allow blockage in the passage. Such blockage can also be obtained by thickening of the plate at its posterior end, or by a stop. The length of the arched plate (20), between its posterior end and its anterior pointed end ("anterior" and "posterior" being defined in reference to the direction of insertion of the plate in the implant) depends on the length of the passage, the positioning and/or orientation of the passage (12) relative to the upper or lower surface of the implant (such as for example evident in the various variants illustrated in FIGS. 6A, 6B, 6C, 6D and 6E) and of the radius of curvature of the plate which is adapted to the trajectory defined by the passage, but this length could also vary as a function of the depth at which the pointed end is to enter the vertebral structures and optionally the presence of trays (3, C) or other anatomical adaptation elements. In this way, in some embodiments, the length of said plate (20) and of said points (21) is configured as a function of the passage such that just the two points project from the implant and penetrate the vertebral structures. Also, this concerns radius of curvature and it is clear that the edges or curved faces of the plate describe one or more radii of curvature. Finally, the passage (12) imposes a curvilinear trajectory on the anchor (2, 2a, 2d) but it in turn can be curved, as illustrated for example in FIGS. 8C and 8D, or rectilinear. When it is rectilinear, it preferably comprises at least two rectilinear portions of different orientations (tangential to a radius of curvature which the plate is to follow), as illustrated for example in FIGS. 8A and 8B. This type of passage in 2 rectilinear portions makes it easier to manufacture the implant by rectilinear bores (one from the passage inlet and one from the outlet), and facilitates passage of the anchor.

In some embodiments, at least one posterior portion of the curved plate (20) comprises a plurality of notches (27) engaging in the wall of the passage (12) of the implant (1) to immobilize the fastening means (2, 2a, 2d) on completion of deployment. Such notches or teeth (27) block the arched plate in the passage. In some embodiments, these notches

Figure 12A:
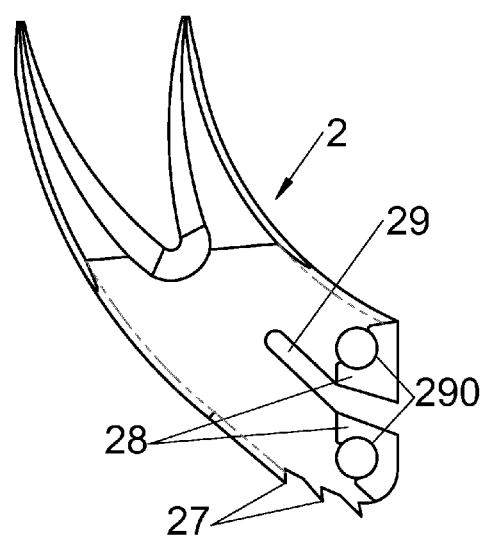
FIGS. 12A and 12B, show, respectively, a profile view and a perspective view, of fastening means according to some embodiments.
Figure 12B:
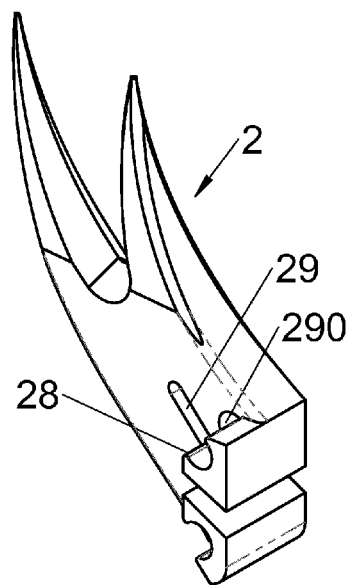
Figure 12C:
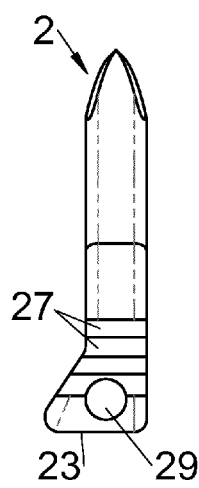
FIGS. 12C, 12D and 12E show, respectively, a plan view from below, a profile view and a perspective view of fastening means according to other embodiments.
Figure 12D:
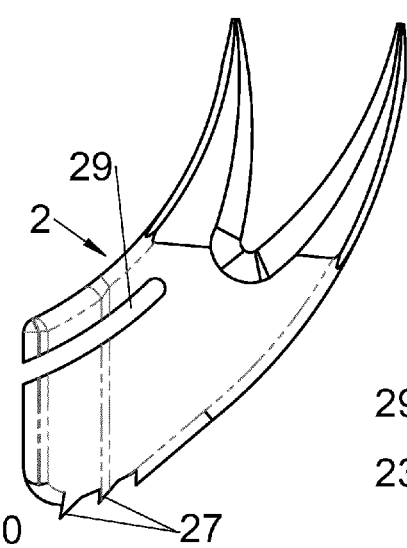
Figure 12E:
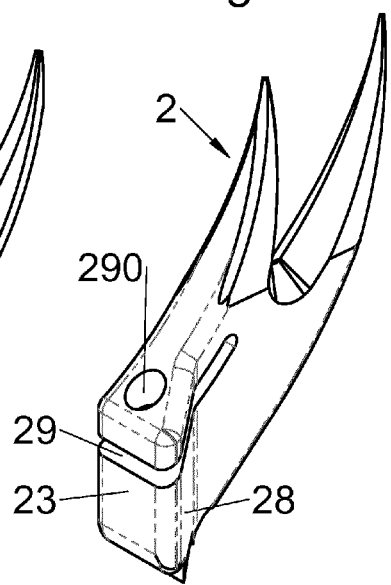
Figure 13A:
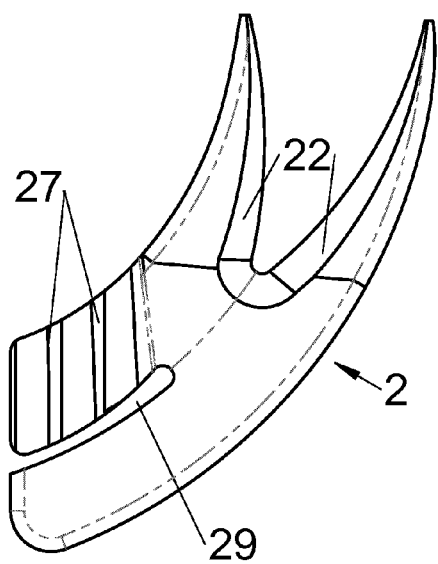
FIGS. 13A, 13B and 13C show, respectively, a profile view, a frontal view and a perspective view of fastening means according to some embodiments.
Figure 13B:
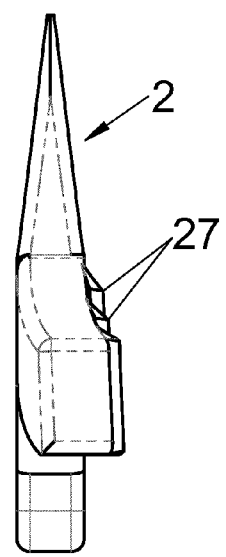
Figure 13C:
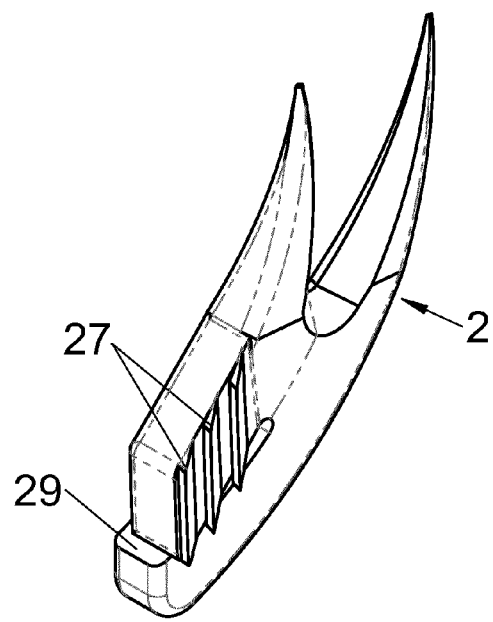
Figure 14A:
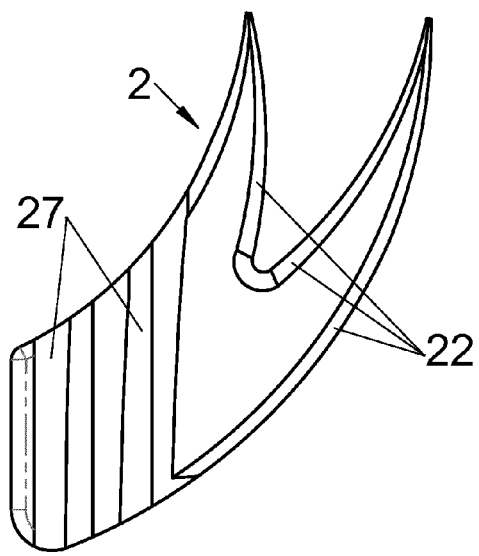
FIGS. 14A, 14B and 14C show, respectively, a profile view, a perspective view and a plan view of fastening means according to some embodiments.
Figure 14B:
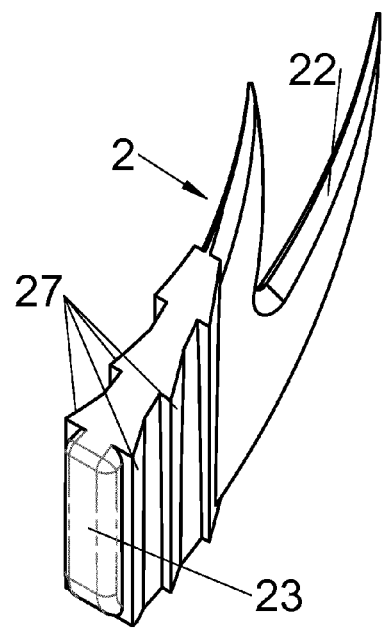
Figure 14C:
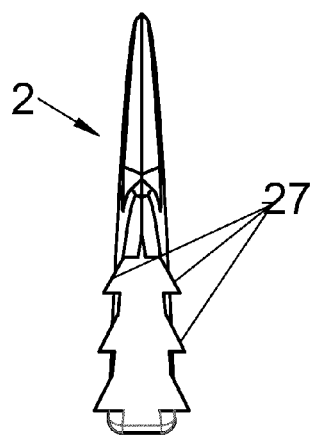
Figure 15A:
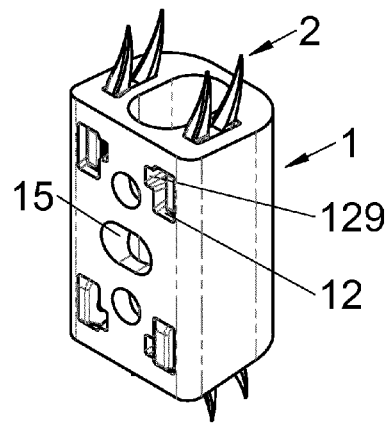
FIG. 15A shows a perspective view of an implant fitted with fastening means according to some embodiments.
Figure 15B:
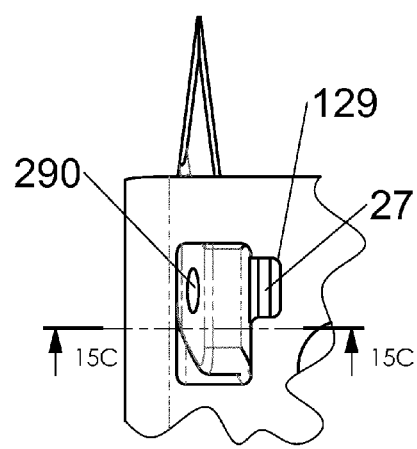
FIGS. 15B and 15C show, respectively, a frontal view and a sectional view according to the sectional plane 15C-15C of FIG. 15B, on the one hand of this same implant fitted with fastening means.
Figure 15C:
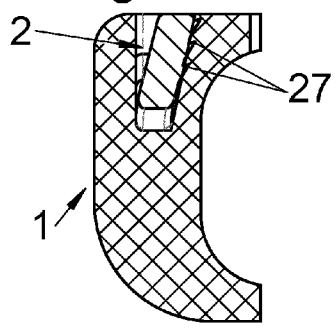
Figure 15D:
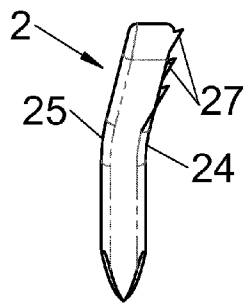
FIGS. 15D and 15E show, respectively, a plan view from below and a perspective view of fastening means according to these embodiments.
Figure 15E:
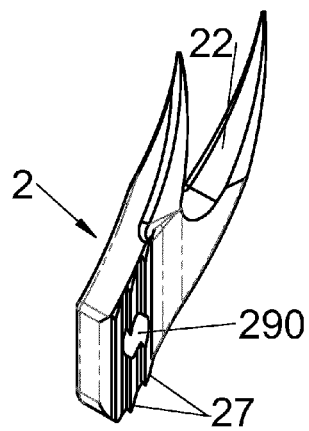
Figure 16A:
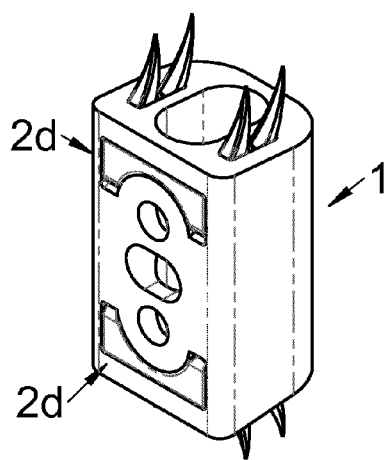
FIG. 16A shows a perspective view of an implant fitted with fastening means according to some embodiments.
Figure 16B:
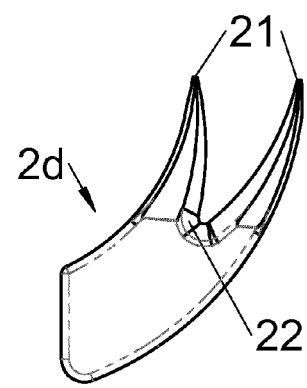
Figure 16C:
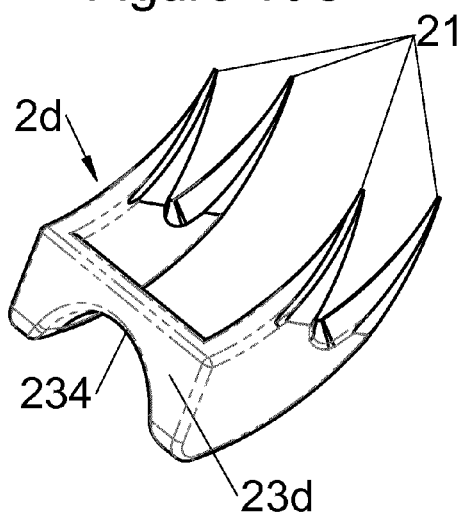
Figure 18A:
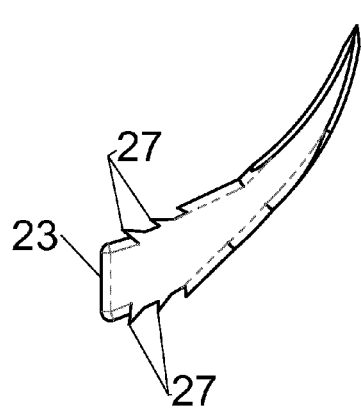
FIGS. 18A and 18B show, respectively, a profile view and a perspective view of fastening means according to some embodiments.
Figure 18B:
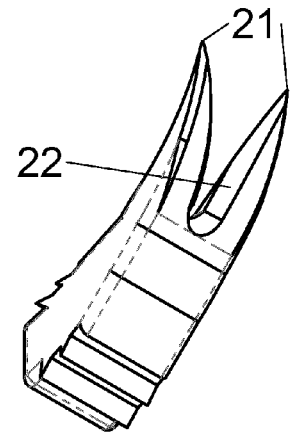
Figure 18C:
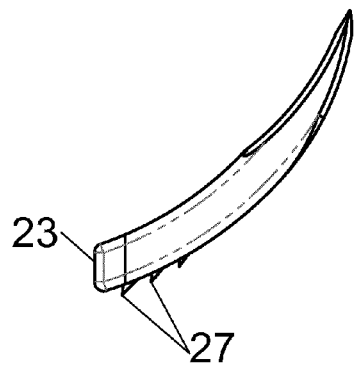
FIGS. 18C, 18D and 18E show, respectively, a profile view, a plan view and a perspective view of fastening means according to other embodiments.
Figure 18D:
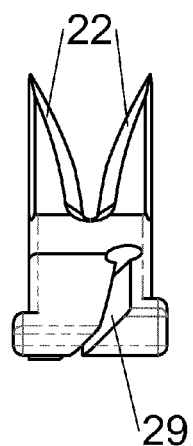
Figure 18E:
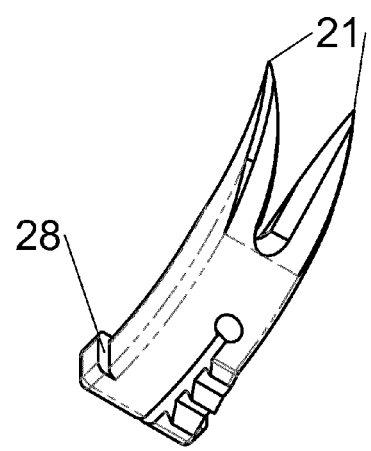
Figure 19A:
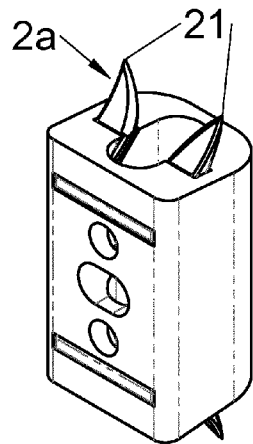
FIGS. 19A, 19B, 19C and 19D show perspective views, respectively, of an implant fitted with fastening means and fastening means alone, according to some embodiments.
Figure 19B:
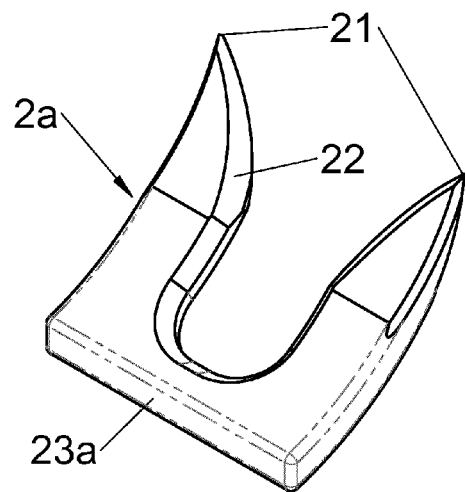
Figure 19C:
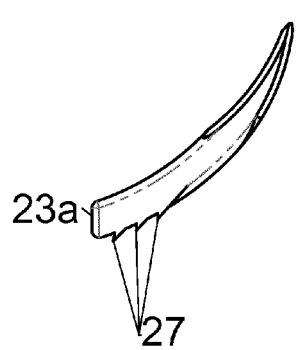
Figure 19D:
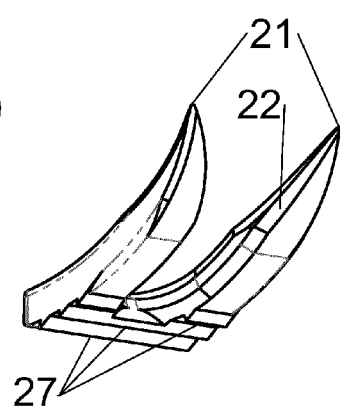
Figure 19E:
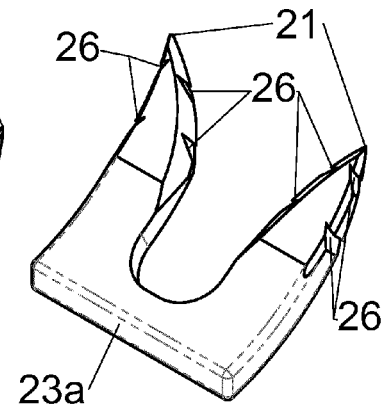
FIG. 19E shows a perspective view of a variant of these fastening means.
Figure 20A:
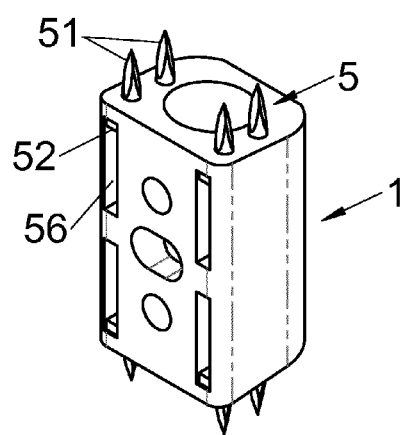
FIGS. 20A, 20B, 20C and 20D show perspective views of an implant and of deployment of its fastening means according to some embodiments, respectively, after deployment, on completion of deployment by means of a spacer, before deployment by means of a stylus and on completion of deployment by means of a stylus of the fastening means.
Figure 20B:
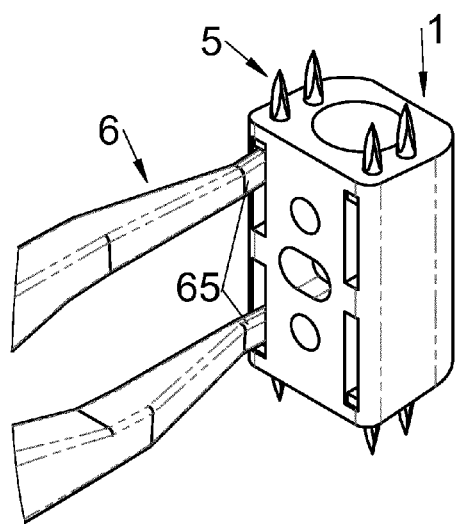
Figure 20C:
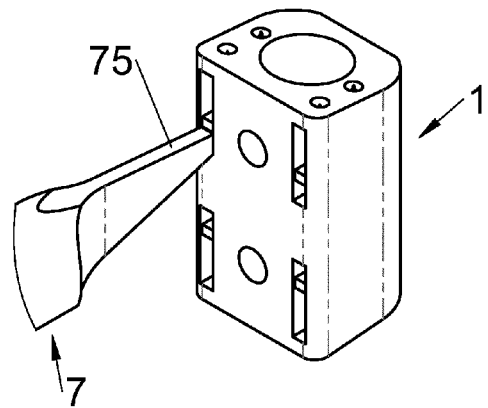
Figure 20D:
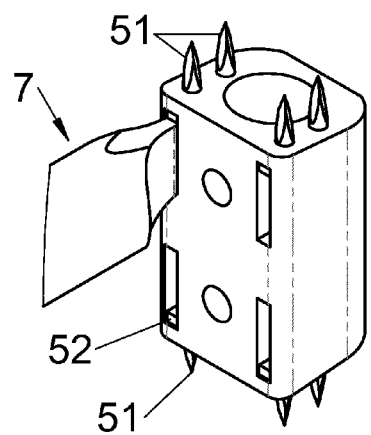
Figure 21A:
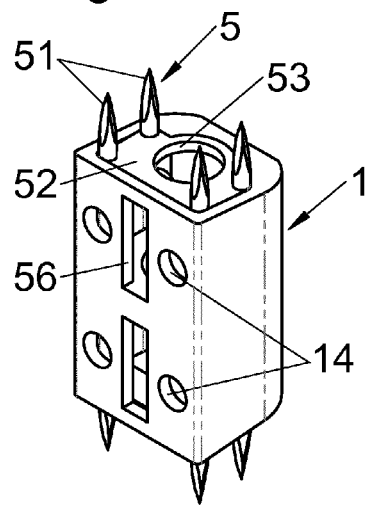
FIGS. 21A, 21B, 21C and 21D show perspective views of an implant and of deployment of its fastening means according to some embodiments, respectively, after deployment, on completion of deployment by means of a stylus, before deployment by means of a spacer and on completion of deployment by means of a spacer.
Figure 21B:
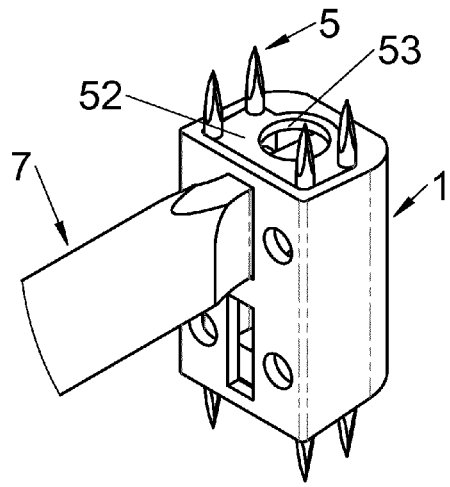
Figure 21C:
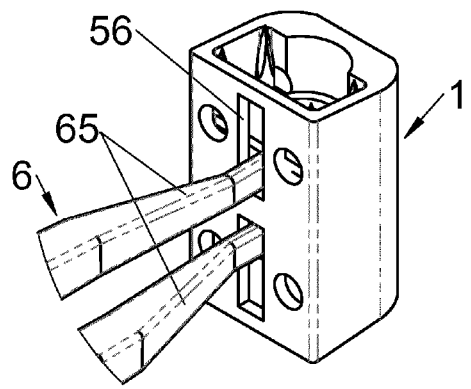
Figure 21D:
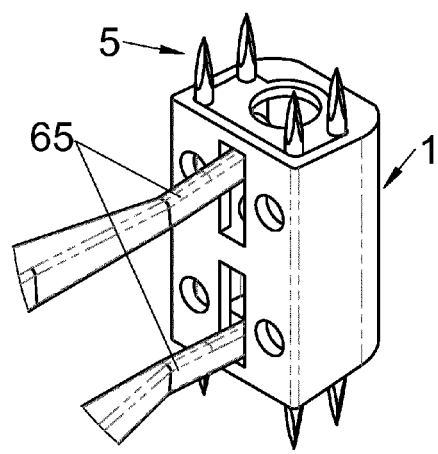
Figure 22A:
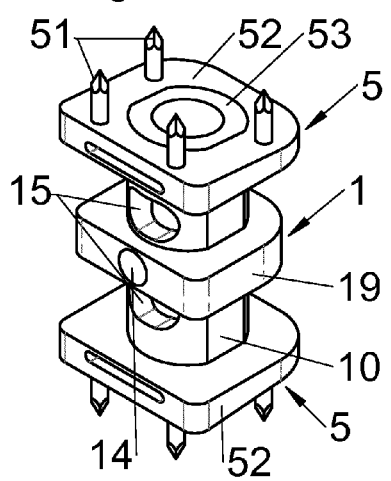
FIGS. 22A, 22B, 22C and 22D show perspective views of an implant and of deployment of its fastening means according to some embodiments, respectively, after deployment, before assembly, during deployment by means of a double stylus and on completion of deployment by means of a double stylus.
Figure 22B:
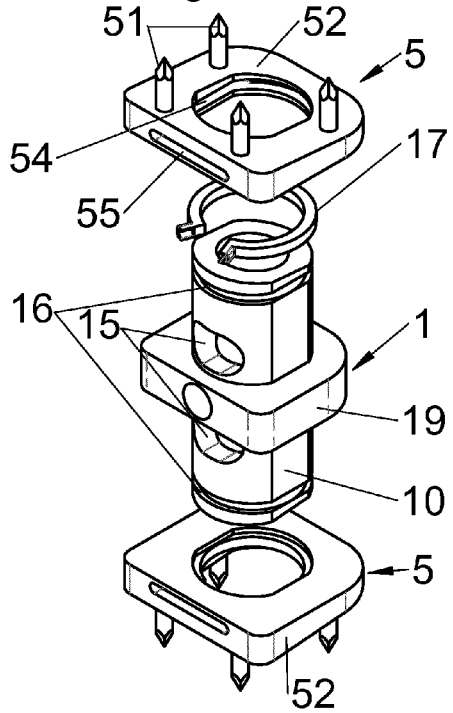
Figure 22C:
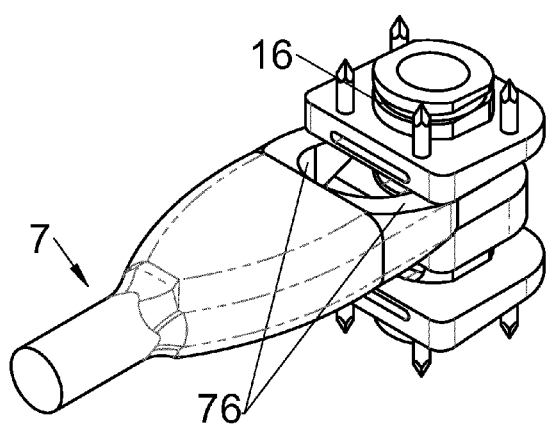
Figure 22D:
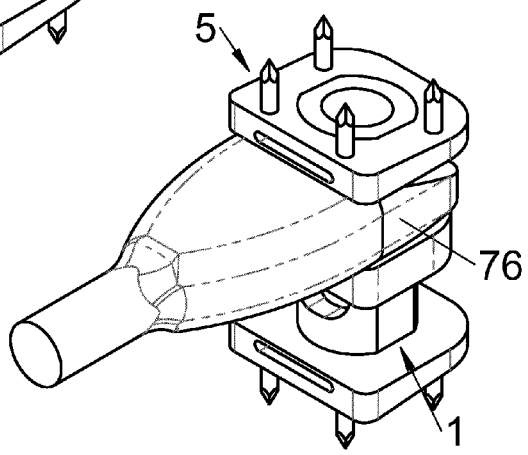
Figure 23A:
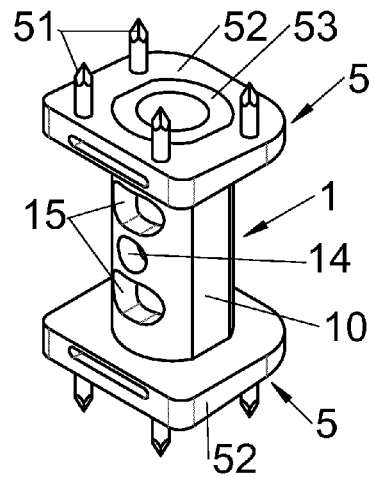
FIGS. 23A, 23B, 23C and 23D show perspective views of an implant and of deployment of its fastening means according to some embodiments, respectively, after deployment, before assembly, during deployment by means of a spacer and on completion of deployment by means of a spacer.
Figure 23B:
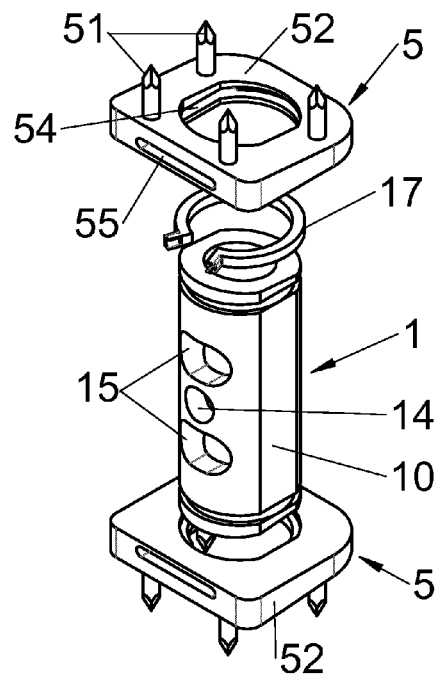
Figure 23C:
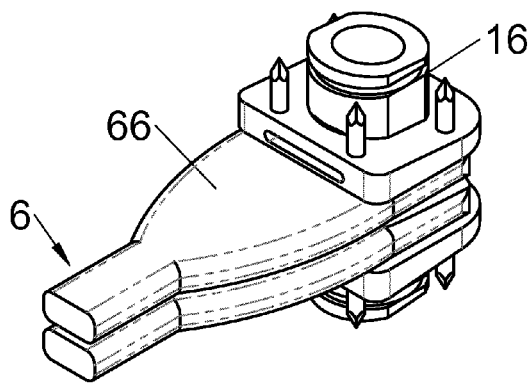
Figure 23D:
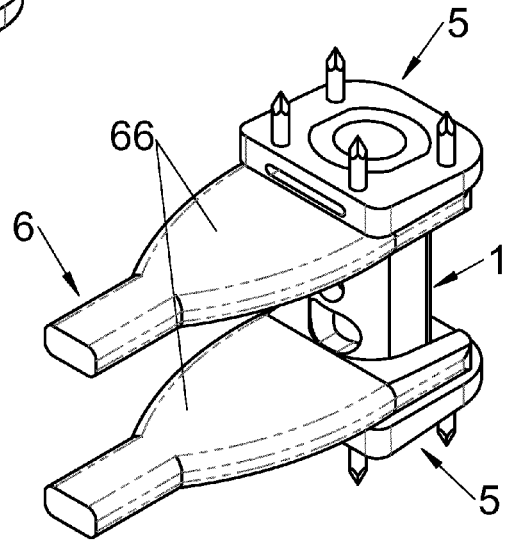
Figure 24A:
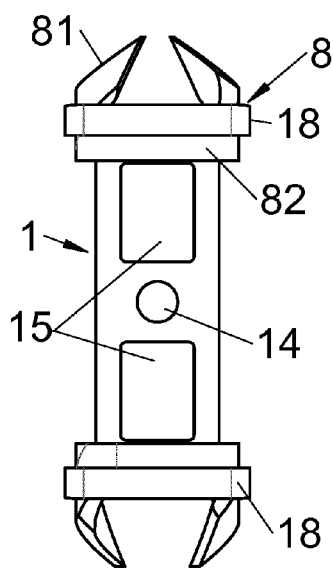
FIGS. 24A and 24B show, respectively, a frontal view and a perspective view of an implant fitted with fastening means according to some embodiments.
Figure 24B:
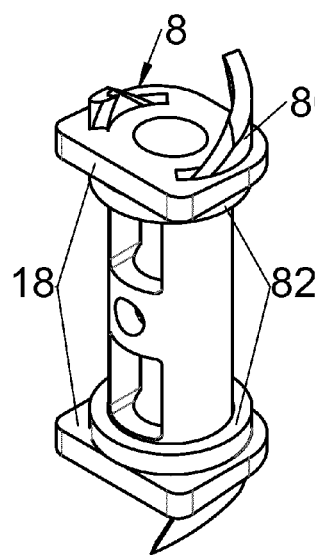
Figure 24C:
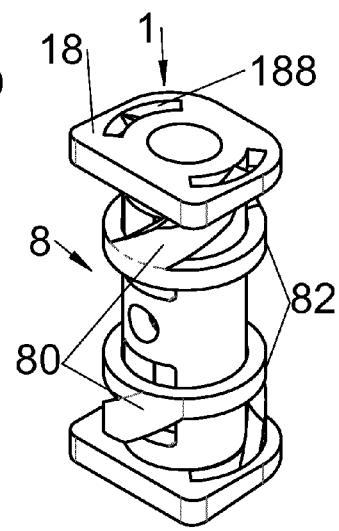
FIG. 24C shows this same implant during deployment of its fastening means.
Figure 24D:
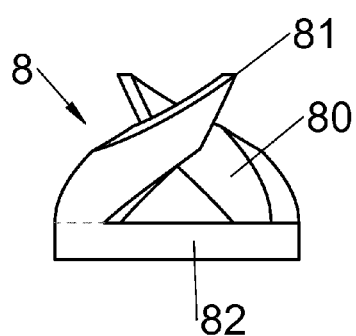
FIGS. 24D and 24E show, respectively, a frontal view and a perspective view of the fastening means of FIGS. 24A, 24B and 24C, FIGS. 25A, 25B and 25C show perspective views of an implant and of deployment of its fastening means according to some embodiments, during deployment of the fastening means, respectively, with a double spacer, a double stylus and an impactor.
Figure 24E:
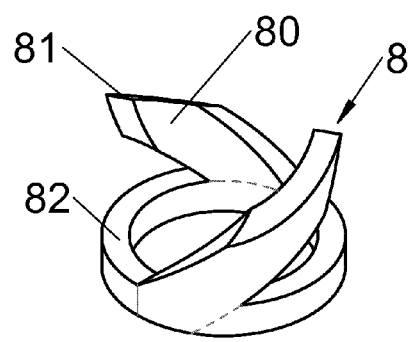

(27) become anchored in a wall of the passage, especially in the case of a PEEK implant and enable immobilization of the plate in the implant (in the direction in which the anchor is removed and optionally also in the direction of the penetrated vertebral structures). These notches can be provided on the concave edge but preferably on the convex edge which provides better support, as illustrated for example in FIGS. 11 (A to E), 12 (A, C and D) and 8C, and/or on at least one of the plane faces, as illustrated for example in FIGS. 13 (A to C), 14 (A to C) where the notches are on both faces and 15 (B to E). In other embodiments, these notches (27) can be provided on at least one part of the concave face, but preferably the convex face, as illustrated for example in FIG. 17 (B to E), 18 (A to E) or 19C and 19D. In some embodiments, said curved plate (20) comprises, on at least one posterior portion, a slot (29) passing through its entire thickness for disengaging said notches (27) during removal of the fastening means (2, 2a, 2d). This type of arrangement has the advantage of facilitating ablation. According to the position of the notches (27), the slot will be positioned to allow flexion of at least one of the branches separated by the slot (29) to disengage the notches (27). FIGS. 11D, 11E, 12A, 12B, 12D and 12E show examples of such slots. FIGS. 13A and 13C show other examples in which the two branches separated by the slot are not in the same plane: the branch bearing the notches is curved in the direction of the notches, for better gripping of the notches (27) in the wall of the passage (12) of the implant. Pushing this branch in the opposite direction facilitates removal. FIGS. 15 (A to E) also show a variant in which no slot is provided, but where the notches (27) are present over a portion of the plate which is curved in the direction of the notches. Pushing (twisting) this posterior portion of the plate, for example by way of a tool penetrating a housing (290) provided for this purpose via access (129) provided in the wall of the passage (12) facilitates ablation. It is noted that this type of ablation housing (290) can be provided in various places, as a function of the position of the notches, as illustrated for example in FIG. 12C. Similarly, FIGS. 12A and 12B show two housings (290) of this type optionally allowing them to be gripped by pliers to bring the two branches towards each other. FIGS. 17D and 17E show another variant of non-coplanar branches where action on at least one of the branches disengages the anchor. FIGS. 18D and 18E show yet another variant where the slot (29) traverses the thickness of the plate but in a plane not perpendicular to the plate such that the slot is oblique in the thickness of the implant. In this way, by clamping the two branches (bringing them towards each other), one of them on which the notches (27) will be provided will straddle the other and free up the notches (27). FIGS. 31 (A to D) and 32 (A and B) show yet another variant where the slot (29) separates the curved plate (20) into two branches which bear notches (27) on their external rectilinear lateral edges (located at the side oppose the slot). This type of arrangement disengages the notches (27) by bringing the two branches towards each other, for example by means of piers gripping the anchor at the level of ergots arranged at the posterior end, for example as shown in FIGS. 32A and 32B.

In some embodiments, said curved plate (20) comprises, in the region of its posterior end, at least one stop surface (28) not parallel to the surface of the plate to limit penetration of the fastening means (2, 2a, 2d) in the implant (1). FIGS. 11 (C to E), 12 (A to E), 17 and 18 show illustrative examples of such stops.

Figure 9A:
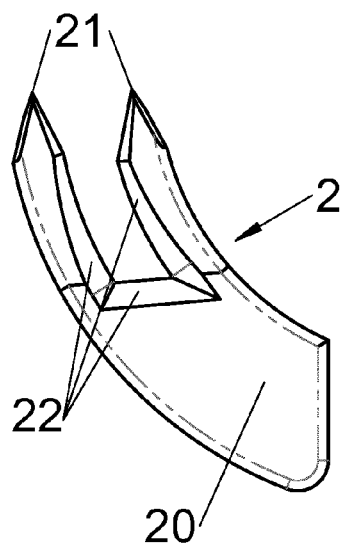
FIGS. 9A, 9B, 9C and 9D show profile views of fastening means according to different embodiments.
Figure 9B:
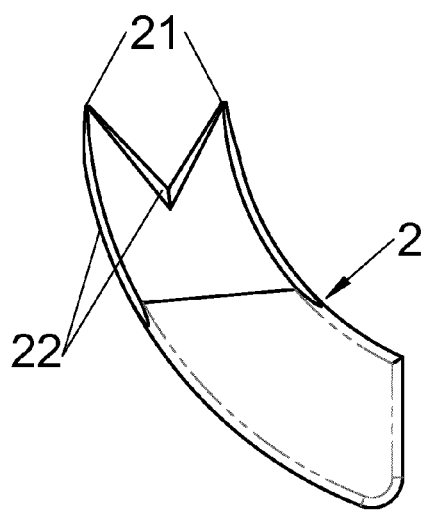
Figure 9C:
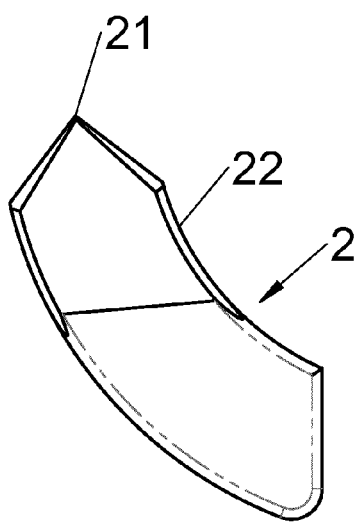
Figure 9D:
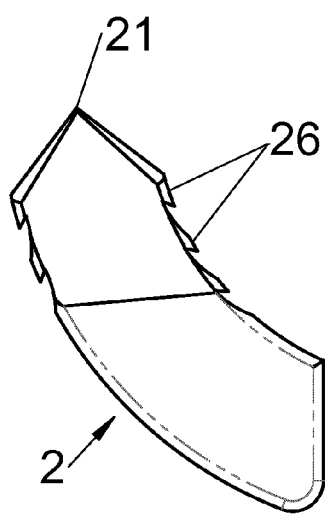
Figure 10A:
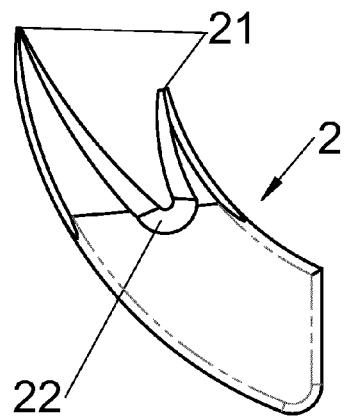
FIGS. 10A and 10B show, respectively, a profile view of fastening means and a sectional view on the one hand of an implant after pre-assembly of these fastening means according to some embodiments.
Figure 10B:
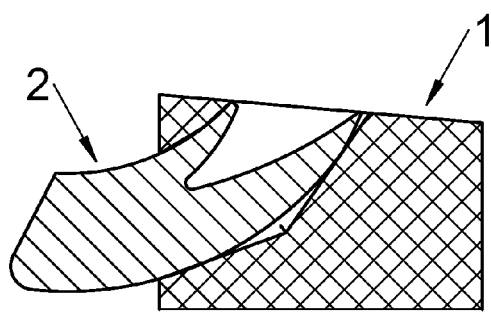
Figure 10C:
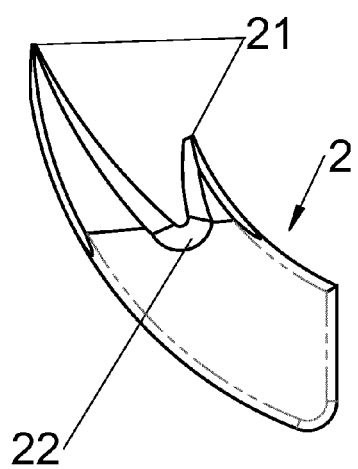
FIGS. 10C and 10D show, respectively, a profile view of fastening means and a sectional view on the other hand of an implant after pre-assembly of these fastening means according to other embodiments.
Figure 10D:
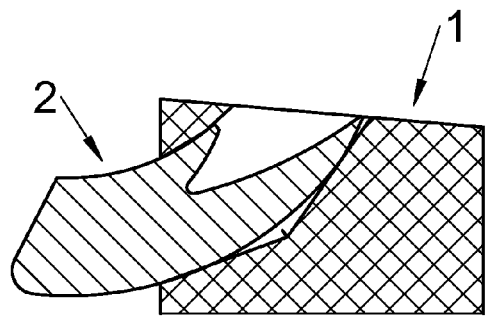
Figure 11A:
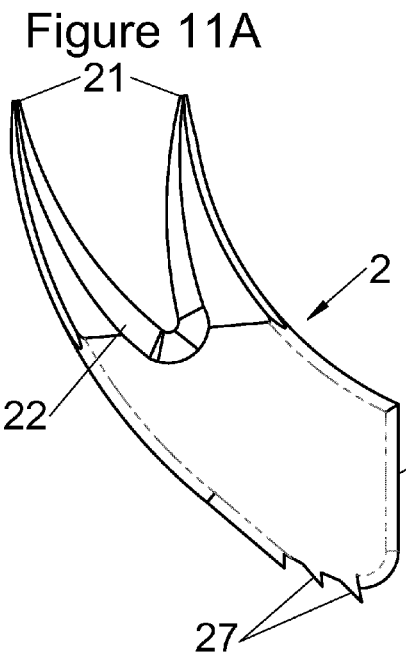
FIGS. 11A and 11B, show, respectively, a profile view and a frontal view, of fastening means according to some embodiments.
Figure 11B:
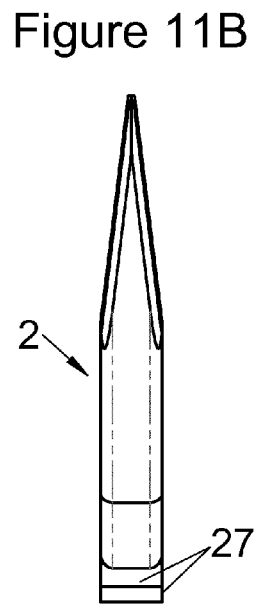
Figure 11C:
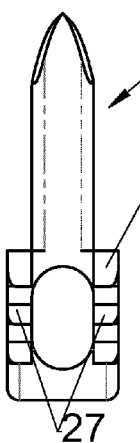
FIGS. 11C, 11D and 11E show, respectively, a plan view from below, a profile view and a perspective view, of fastening means according to other embodiments.
Figure 11D:
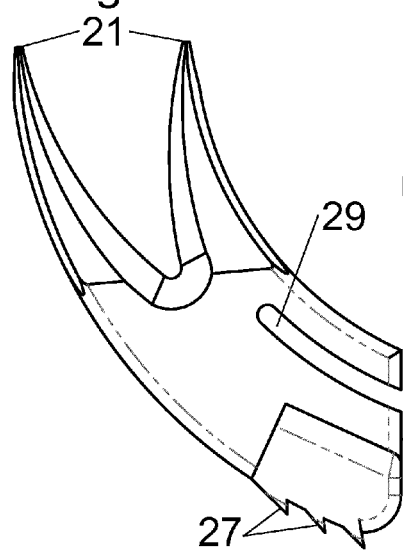
Figure 11E:
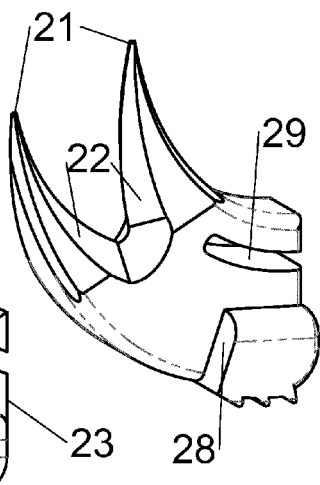

In some embodiments, said pointed end (21) comprises two points (21) separated by at least one sharp portion (22) (e.g., a cutting portion) facilitating penetration in the vertebral structures. Such a sharp portion can also be provided on various edges of the anchor, preferably only on the part designed to penetrate the vertebral structures. For example, FIGS. 9A and 9B show sharp portions (22) on several edges of the plate (20). Similarly, in FIGS. 9C and 9D where the anchor has one point (21) only, sharp edges (22) facilitate insertion of the anchor. It is evident that the points of the same plate (20) cannot have the same length, such that one of them exits from the implant before the other, for example as illustrated in FIGS. 10C and 10D (by comparison with FIGS. 10A and 10B).

In some embodiments, said curved plate (20) comprises, on an anterior portion designed to penetrate the vertebral structures, a plurality of teeth (26), notches or indentations to improve retention of the anchor in the penetrated tissues. FIGS. 9D, 19E, 31B, 31C and 31D show illustrative and non-limiting examples of such teeth (26).

In some embodiments, illustrative and non-limiting examples of which are shown in FIGS. 19 (A to E) and 16 (A to C), the fastening means (2a, 2d) with a curved plate in fact comprise several curved plates joined by a link (23a, 23d), for example, such as a plate or a stick perpendicular to the planes of the curved plates, optionally with irregularities in form (234) to match other elements of the implant. This type of arrangement multiplies the anchoring points and benefits from the advantage given by the plate form offering better stability than narrower structures. It is evident in the figures that the two curved plates are parallel to each other, but that they could be provided not parallel, i.e. even perpendicular to optimize resistance to movement once planted in the vertebral structures.

Figure 30A:
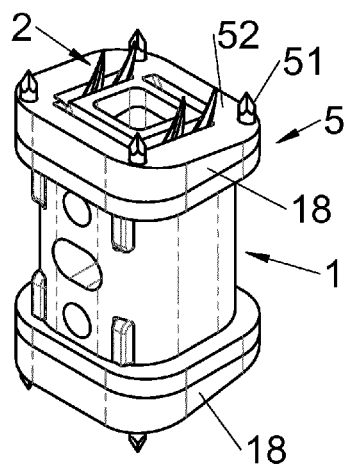
FIGS. 30A and 30B show perspective views of an implant and of deployment of its fastening means according to some embodiments, respectively, after and during deployment.
Figure 30B:
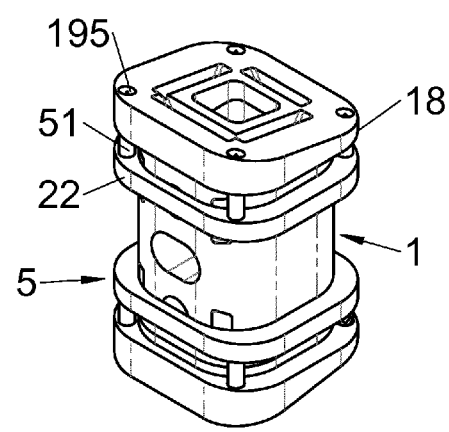
Figure 30C:
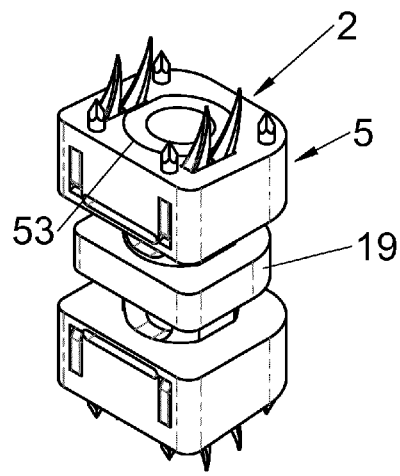
FIGS. 30C and 30D show perspective views of an implant and of deployment of its fastening means according to other embodiments, respectively, after and during deployment.

The foregoing shows that various embodiments, in particular for the anchors with arched plates, permits numerous variants and that the examples provided are illustrative only and that the terms used to define the characteristics must not be interpreted as limiting but rather in their functional definition. Also, the present disclosure details several embodiments of the fastening or anchoring means but also concern any combination thereof. In particular, in some embodiments, it is useful to use at least two fastening means for each of the vertebral structure between which the implant is intended to be inserted. The present disclosure thus also concerns a fastening system for implants comprising at least two fastening means. More specifically, in the case of corpectomy, it is useful to have such fixation by more than one fastening or anchoring mean, because several physiological structures have been removed from the patient and a better stabilization preferably has to be achieved. Such stabilization is obtained by a combination of at least two fastening means as described in the present disclosure for each vertebral structure. It should be noted that one fastening means of the present disclosure could be combined with any other known fastening means, such as screws or any other device, although it will be preferred to combine two anchoring means as in the present disclosure. FIGS. 30A and 30C show two illustrative and non-limiting examples of such combination. Furthermore, the (at least) two fastening means can either be identical or different from each other and may have orientations parallel to each other or not. A non-parallel orientation generally is useful for a better stabilization and the fastening means can also have different length so that their part protruding from the implant and penetrating the vertebral structures are offset from each other, so as to further improve the stabilization.

Instrumentation

This disclosure also relates to instrumentation for insertion of the implant and/or impingement of the fastening means.

In some embodiments, illustrative and non-limiting examples of which are shown in FIGS. 27 (A to D), instrumentation comprises an implant holder (P) which preferably cooperates with the hooking means (14) provided on the implant. These means can be housings or any type of structure for the implant to be held by the instrument. On the other hand, instrumentation can comprise at least one impactor (I) for having anchors with a curved plate penetrate the vertebral structures. Advantageously, the implant holder (P) and the impactor (I) are complementary to each other such that the implant holder (P) holding the implant allows, or even guides, the sliding of the impactor, for example as shown in FIGS. 27C and 27D. For example, the implant holder may comprise a head (P2) bordered by at least one wing (P1) on which can rest at least one branch of the impactor guided in this way towards the implant. Advantageously, the impactor (I) can comprise at least two branches (12) for impacting at least two anchors through the implant at the same time, for example on either side of the head (P2) of the implant holder (P) which provides a reliable guide rail.

Figure 26A:
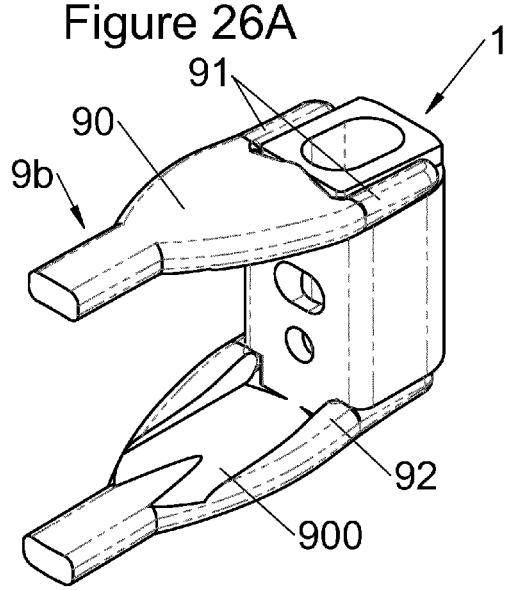
FIG. 26B shows a perspective view of the implant of FIG. 26A and FIGS. 26C and 26D show, respectively, a profile view and a perspective view, of the insertion spacer of the implant of FIGS. 26A and 26B, FIGS. 27A, 27B, 27C and 27D show perspective views of an implant and of deployment of its fastening means according to some embodiments, respectively, after insertion of the fastening means, before deployment during the holding of the implant by an implant holder, during deployment by an impactor and after deployment.
Figure 26B:
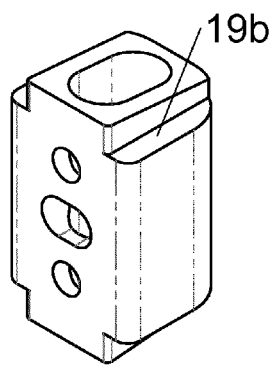
Figure 26C:
Figure 26D:
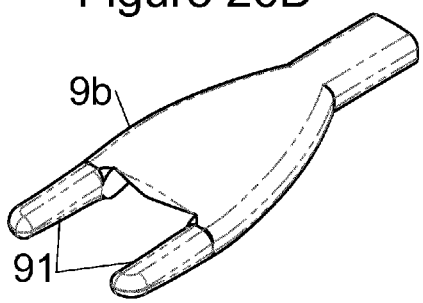
Figure 26E:
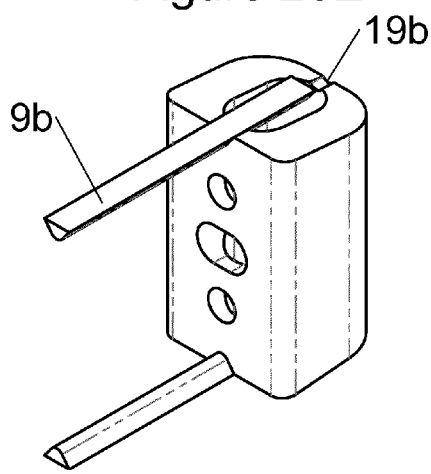
Figure 27A:
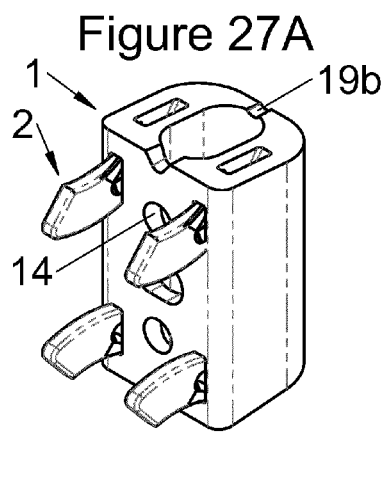
Figure 27B:
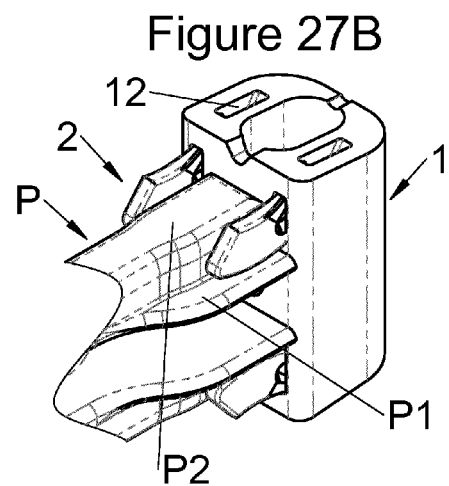
Figure 27C:
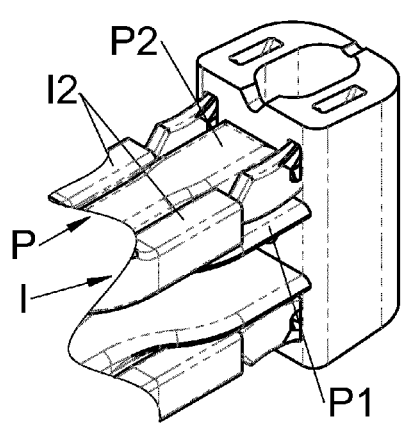
Figure 27D:
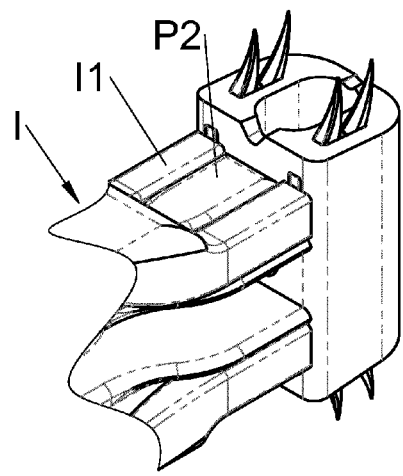

According to various embodiments, the instrumentation can comprise at least one distractor (or distraction clamp) on the one hand to at least maintain or even enlarge (even if distractors with big contact surface are generally preferred) the space left by the removed vertebral segment, and, on the other hand facilitate placement of the implant (1). FIGS. 26A, 26C and 26D show an example of a distractor (9b) comprising a plate (90) having a surface (900) configured to receive and guide the implant to the implant space (between the vertebral structures), for example by means of branches (91) supporting the vertebral structures and forming rails along which shoulders (19b) of the implant are guided, for example as shown in FIG. 26B. FIG. 26E shows another example of a distractor (9b) comprising a branch supporting the vertebral structures and forming a rail along which the implant is guided, for example by way of grooves (19b) on its upper and lower surfaces. These types of spacers facilitate implantation and enable insertion of the implant, especially with an implant holder (P), in particular of the type of those described in the present application, and even the use of an impactor (1), a spacer (6) or a stylus (7) as described in the present application. This disclosure therefore also relates to instrumentation comprising all or part of these various tools or instruments.

At least in some embodiments described in the present application, it is evident that the arrangement of the fastening means, the implant and the instrumentation fix the implant by means of at least two fastening means in the vertebral structures located above and below (in the spine) the vertebral segment replaced by the implant. In fact, by means of a double impactor or two impactors (1) sliding above and below an implant holder (P), it is possible especially via configuration of various embodiments of the anchors of the present application to anchor at least two anchors at the same time, in the same vertebral structure or each in one of the upper and lower structures on the treated vertebral segment, because the trajectories of these anchors, even when they are curvilinear, do not cross and the configuration of the implant (especially the footprint) is compatible with such simultaneous anchoring of the two anchors.

Figure 30D:
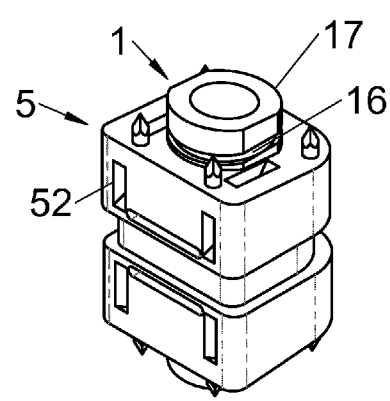
Figure 31A:
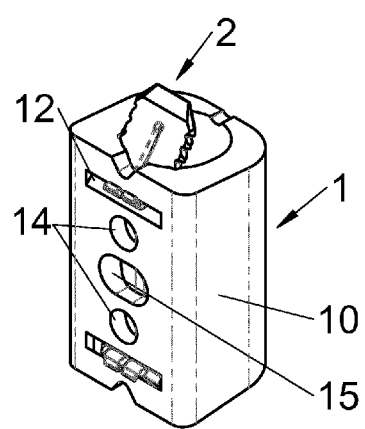
FIG. 31A shows a perspective view of an implant fitted with fastening means according to some embodiments.
Figure 31B:
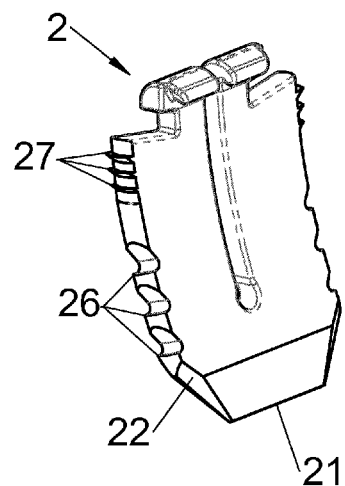
FIGS. 31B, 31C and 31D show, respectively, a perspective view, a profile view and a frontal view of the fastening means of the implant of FIG. 31A.
Figure 31C:
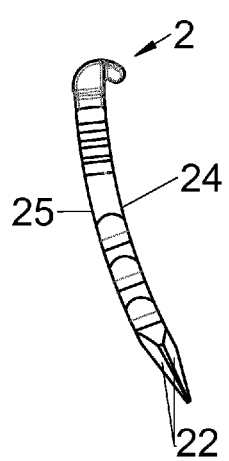
Figure 31D:
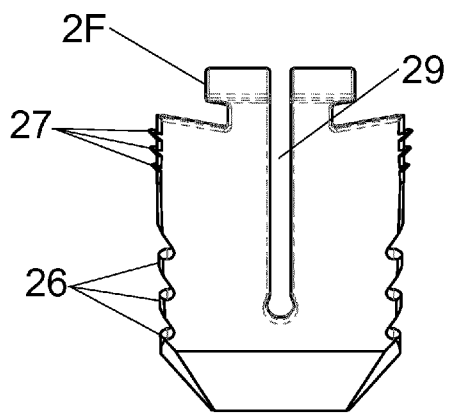

The present application describes various technical characteristics and advantages in reference to the figures and/or embodiments. The expert will know that the technical characteristics of a given embodiment can in fact be combined with characteristics of another embodiment unless otherwise stipulated or it is evident that these characteristics are incompatible or the combination does not supply a solution to at least one of the problems technical mentioned in the present application. Also, the technical characteristics described in a given embodiment can be isolated from the other characteristics of this mode unless otherwise stipulated. In this way, for example, FIGS. 30A, 30B, 30C and 30D show combinations of fastening means of various embodiments on the same implant. FIGS. 30A and 30B show for example a plate (52) sliding about the implant and comprising points (51) which pass through holes (195) of a locking crown (18) of the sliding and arched plates (20) which are then inserted and preferably slightly project from the peripheral wall of the implant to lock the sliding plate (52) against the crown (18), ensuring complete blocking of the points (52) in the vertebral structures. FIGS. 30C and 30D show other examples of combination in which the sliding plate (52) (locked by clamping clip) actually forms a thick crown comprising passages arranged for taking up arched plates (20). Once the points (51) of the sliding plate (52) are planted in the vertebral structures, the arched plates are added to reinforce the fixing.

It must be evident for the person skilled in the art that this disclosure permits embodiments in numerous other specific forms without departing from the field of application of this disclosure. Consequently, the present embodiments must be considered by way of illustration, but can be modified in the field defined by the scope of the attached claims, and the claims based on this disclosure must not be limited to the details given hereinabove.

The invention claimed is:

1. An implant for corpectomy of a spine having a longitudinal axis, the implant having a longitudinal axis and being sized to replace a removed segment of the spine with the longitudinal axis of the implant disposed generally parallel to the longitudinal axis of the spine, the implant comprising a peripheral wall; an upper spinal contact surface; a lower spinal contact surface; upper and lower fasteners each having a retracted position and a deployed position, each of the upper and lower fasteners comprising a plate that remains in contact with the peripheral wall when the fastener is deployed, and each of the upper and lower fasteners comprising a sharpened end configured to penetrate an unremoved spinal segment during deployment to retain the implant to that unremoved spinal segment, with the sharpened end of the upper fastener projecting from the upper spinal contact plate and the sharpened end of the lower fastener projecting from the lower spinal contact plate.

2. The implant of claim 1 in which deployment of a fastener causes that fastener to slide in a direction generally parallel to the longitudinal axis of the implant.

3. The implant of claim 2 in which the fastener slides within the peripheral wall during deployment.

4. The implant of claim 1 in which the plate of one of the fasteners is oriented generally perpendicular to the longitudinal axis of the implant, the sharpened end of that fastener extends from a body projecting from that plate generally parallel to the longitudinal axis of the implant, that plate is disposed in a housing contained within the peripheral wall, and a periphery of that plate remains in contact with a wall of the housing when that fastener is deployed.

5. The implant of claim 4, in which that housing has a width at least as large as a width of that plate and a height at least as great as a height of that anchor, and that housing terminates at one of the spinal contact surfaces with a hole receiving the sharpened part of that fastener during deployment.

6. The implant of claim 2, in which one of the fasteners slides along an exterior portion of the peripheral wall.

7. The implant of claim 6, in which the plate of the fastener that slides along an exterior portion of the peripheral wall has an opening at least as large as the peripheral wall, and a retainer engages that plate and the peripheral wall to hold the fastener in the deployed position.

8. The implant of claim 1 in which deployment of a fastener causes that fastener to slide to rotate about an axis generally parallel to the longitudinal axis of the implant.

9. A device for corpectomy of a spine having a longitudinal axis and comprising:
an implant having a longitudinal axis and being sized to replace a removed segment of the spine with the longitudinal axis of the implant disposed generally parallel to the longitudinal axis of the spine, the implant comprising a peripheral wall, a spinal contact surface disposed an at an end of the implant along the longitudinal axis of the implant and configured to contact a spinal surface of an unremoved segment of the spine, a peripheral wall around the implant along the longitudinal axis of the implant, and a curvilinear passage extending from the peripheral wall to the spinal contact surface; and
an anchor comprising a body with curvilinear shape complementary to a shape of the curvilinear passage, a leading end sharpened to facilitate penetration of the unremoved segment of the spine, and a trailing end capable of receiving a force to urge the leading end into the unremoved segment of the spine, the anchor having a deployed position resulting from movement of the leading end through the passage until the leading end projects from the spinal contact surface and the trailing end is disposed proximal to the peripheral wall.

10. The device of claim 9 in which the trailing end of the anchor comprises plural notches configured to retain the anchor in the deployed position.

11. The device of claim 10 in which the anchor comprises a slot oriented in a longitudinal direction along the trailing end, the slot allowing deflection of the portion of the trailing end of the anchor comprising the plural notches to release the anchor from the deployed position.

12. The device of claim 9 in which the anchor comprises a stop surface configured to engage a complementary stop surface disposed along passage, with that engagement stopping the anchor in the deployed position.

13. The device of claim 9 in which the anchor comprises plural sharpened projections at the leading end, and only the plural sharpened projections at the leading end project from the spinal contact surface when the anchor is in the deployed position.

14. The device of claim 9 in which the implant comprises plural individual segments that are configured to be stacked along the longitudinal axis of the implant to form an implantable unit.

15. The device of claim 14 further comprising a medial segment having a peripheral wall separating a pair of segments each having a spinal contact surface and a curvilinear passages extending from the peripheral wall to the spinal contact surface.

16. The device of claim 9 in which the implantable unit comprises a hollow core extending along the longitudinal axis of the implant from an opening in one of the segments having a spinal contact surface and the other of the segments having a spinal contact surface.

17. The device of claim 16 in which the peripheral wall of at least one segment comprises a conduit for placement of a fusion promoting compound into the hollow core.

18. A corpectomy cage and anchor for treating a spine comprising an upper housing, a medial housing, and a lower housing, and further comprising:
an upper surface on the upper housing configured to contact a lower surface of an upper segment of the spine; a lower surface on the upper housing having a dovetailed recess and a shape that complements a shape of an upper surface of the medial housing to interlock the upper housing and the medial housing when the cage is fully assembled; a peripheral wall disposed between the upper surface of the upper housing and the lower surface of the upper housing and defining a cavity within the upper housing configured to receive a fusion inducing compound; and a passage having a generally rectangular cross section and extending along a curvilinear trajectory from the peripheral wall of the upper housing to the upper surface of the upper housing;
a lower surface on the lower housing configured to contact an upper surface of a lower segment of the spine; an upper surface on the lower housing having a dovetailed recess and a shape that complements a shape of a lower surface of the medial housing to interlock the lower housing and the medial housing when the cage is fully assembled; a peripheral wall disposed between the upper surface of the lower housing and the lower surface of the lower housing and defining a cavity within the lower housing configured to receive a fusion inducing compound; and a passage having a generally rectangular cross section and extending along a curvilinear trajectory from the peripheral wall of the lower housing to the lower surface of the lower housing;
a dovetailed projection extending along the upper surface of the medial housing configured to interlock with the dovetailed recess of the upper housing; a dovetailed projection extending along the lower surface of the medial housing configured to interlock with the dovetailed recess of the lower housing; and a peripheral wall disposed between the upper surface of the medial housing and the lower surface of the medial housing and defining a cavity within the medial housing configured to interconnect the cavity in the upper housing and the cavity in the lower housing when the cage is fully assembled and to receive a fusion inducing compound;
an upper anchor comprising an upper anchor body with a rectangular cross section having a height and a width less than the height, the rectangular cross section extending along a portion of the length of the anchor in a curvilinear trajectory from a leading end of the upper anchor body to a trailing end of the upper anchor body, the rectangular cross section defining a pair of generally planar external surfaces along each side of the upper anchor body in the direction of the height and a pair of curvilinear external surfaces along each side of the upper anchor body in the direction of the width, with an upper one of the pair of curvilinear surfaces being concave along the curvilinear trajectory from the leading end of the upper anchor body to the trailing end of the upper anchor body and a lower one of the pair of curvilinear surfaces being convex along the curvilinear trajectory from the leading end of the upper anchor body to the trailing end of the upper anchor body, the curvilinear trajectory of the rectangular cross section of the upper anchor body being complementary to the curvilinear trajectory of the passage in the upper housing such that the upper anchor can pass through the peripheral wall of the upper housing into the passage in the upper housing; a sharpened projection extending from the leading end of the upper anchor body, the sharpened projection configured to penetrate the lower surface of the upper segment of the spine; a stop surface protruding from the trailing end of the upper anchor body configured to engage a complementary stop surface of the passage in the upper housing disposed proximal to the peripheral wall of the upper housing and stop transit of the upper anchor through the passage in the upper housing when the stop surface protruding from the trailing end of the upper anchor body contacts the complementary stop surface of the passage in the upper housing; and a length sufficient for the sharpened projection of the upper anchor to extend beyond upper surface of the upper housing when the upper anchor is fully inserted into the passage in the upper housing and the stop surface of the upper anchor contacts the complementary stop surface of the passage in the upper housing; and a lower anchor comprising a lower anchor body with a rectangular cross section having a height and a width less than the height, the rectangular cross section extending along a portion of the length of the anchor in a curvilinear trajectory from a leading end of the lower anchor body to a trailing end of the lower anchor body, the rectangular cross section defining a pair of generally planar external surfaces along each side of the lower anchor body in the direction of the height and a pair of curvilinear external surfaces along each side of the lower anchor body in the direction of the width, with a lower one of the pair of curvilinear surfaces being concave along the curvilinear trajectory from the leading end of the lower anchor body to the trailing end of the lower anchor body and an upper one of the pair of curvilinear surfaces being convex along the curvilinear trajectory from the leading end of the lower anchor body to the trailing end of the lower anchor body, the curvilinear trajectory of the rectangular cross section of the lower anchor body being complementary to the curvilinear trajectory of the passage in the lower housing such that the lower anchor can pass through the peripheral wall of the lower housing into the passage in the lower housing; a sharpened projection extending from the leading end of the lower anchor body, the sharpened projection configured to penetrate the upper surface of the lower segment of the spine; a stop surface protruding from the trailing end of the lower anchor body configured to engage a complementary stop surface of the passage in the lower housing disposed proximal to the peripheral wall of the lower housing and stop transit of the lower anchor through the passage in the lower housing when the stop surface protruding from the trailing end of the lower anchor body contacts the complementary stop surface of the passage in the lower housing; and a length sufficient for the sharpened projection of the lower anchor to extend beyond lower surface of the lower housing when the lower anchor is fully inserted into the passage in the lower housing and the stop surface of the lower anchor contacts the complementary stop surface of the passage in the lower housing.

19. The corpectomy cage of claim 18 in which the upper anchor comprises a notch disposed proximal to the trailing end of the upper anchor body on the convex one of the curvilinear external surfaces and configured to retain the upper anchor in the passage extending from the peripheral wall of the upper housing to the upper surface of the upper housing; and the lower anchor comprises a notch disposed proximal to the trailing end of the lower anchor body on the convex one of the curvilinear external surfaces and configured to retain the lower anchor in the passage extending from the peripheral wall of the lower housing to the lower surface of the lower housing.

\* \* \* \* \*